United States Patent
Hunter et al.

(10) Patent No.: US 8,328,755 B2
(45) Date of Patent: Dec. 11, 2012

(54) CONTROLLED NEEDLE-FREE TRANSPORT

(75) Inventors: Ian W. Hunter, Lincoln, MA (US); Andrew J. Taberner, Lexington, MA (US); Brian D. Hemond, Lexington, MA (US); Dawn M. Wendell, Farmington, CT (US); Nora Catherine Hogan, Boston, MA (US); Nathan B. Ball, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 60 days.

(21) Appl. No.: 12/906,525

(22) Filed: Oct. 18, 2010

(65) Prior Publication Data

US 2011/0257626 A1    Oct. 20, 2011

Related U.S. Application Data

(60) Division of application No. 11/354,279, filed on Feb. 13, 2006, now Pat. No. 7,833,189, which is a continuation of application No. 11/352,916, filed on Feb. 10, 2006, now abandoned.

(60) Provisional application No. 60/652,483, filed on Feb. 11, 2005.

(51) Int. Cl.
*A61M 5/30* (2006.01)
(52) U.S. Cl. .............................................. 604/68
(58) Field of Classification Search .............. 604/65–68, 604/70–71, 500, 503, 511
See application file for complete search history.

(56) References Cited

U.S. PATENT DOCUMENTS

| 2,194,535 A | 3/1940 | Von Delden |
| 2,550,053 A | 4/1951 | Ferguson |
| 3,057,349 A | 10/1962 | Ismach |
| 3,788,315 A | 1/1974 | Laurens |
| 3,923,060 A | 12/1975 | Ellinwood, Jr. |

(Continued)

FOREIGN PATENT DOCUMENTS

DE    201 05 183 U1    6/2002

(Continued)

OTHER PUBLICATIONS

International Search Report for Int'l Application No. PCT/US2006/004899; Date Mailed: Nov. 17, 2006.

(Continued)

*Primary Examiner* — Christopher D Koharski
(74) *Attorney, Agent, or Firm* — Hamilton, Brook, Smith & Reynolds, P.C.

(57) ABSTRACT

A needle-free transdermal transport device for transferring a substance across a surface of a biological body includes a reservoir for storing the substance, a nozzle in fluid communication with the reservoir and a controllable electromagnetic actuator in communication with the reservoir. The actuator, referred to as a Lorentz force actuator, includes a stationary magnet assembly and a moving coil assembly. The coil assembly moves a piston having an end portion positioned within the reservoir. The actuator receives an electrical input and generates in response a corresponding force acting on the piston and causing a needle-free transfer of the substance between the reservoir and the biological body. The magnitude, direction and duration of the force are dynamically controlled (e.g., servo-controlled) by the electrical input and can be altered during the course of an actuation cycle. Beneficially, the actuator can be moved in different directions according to the electrical input.

7 Claims, 19 Drawing Sheets

U.S. PATENT DOCUMENTS

| | | | |
|---|---|---|---|
| 4,108,177 A | 8/1978 | Pistor | |
| 4,552,559 A | 11/1985 | Donaldson et al. | |
| 4,592,742 A | 6/1986 | Landau | |
| 5,074,843 A | 12/1991 | Dalto et al. | |
| 5,116,313 A | 5/1992 | McGregor | |
| 5,347,186 A | 9/1994 | Konotchick | |
| 5,354,273 A | 10/1994 | Hagen | |
| 5,389,085 A | 2/1995 | D'Alessio et al. | |
| 5,405,614 A | 4/1995 | D'Angelo et al. | |
| 5,425,715 A | 6/1995 | Dalling et al. | |
| 5,505,697 A | 4/1996 | McKinnon, Jr. et al. | |
| 5,533,995 A | 7/1996 | Corish et al. | |
| 5,578,495 A | 11/1996 | Wilks | |
| 5,611,784 A | 3/1997 | Barresi et al. | |
| 6,030,399 A | 2/2000 | Ignotz et al. | |
| 6,090,790 A | 7/2000 | Eriksson | |
| 6,126,629 A | 10/2000 | Perkins | |
| 6,132,385 A | 10/2000 | Vain | |
| 6,203,521 B1 | 3/2001 | Menne et al. | |
| 6,288,519 B1 | 9/2001 | Peele | |
| 6,317,630 B1 | 11/2001 | Gross et al. | |
| 6,319,230 B1 | 11/2001 | Palasis et al. | |
| 6,939,323 B2 | 9/2005 | Angel et al. | |
| 7,032,443 B2 | 4/2006 | Moser | |
| 7,425,204 B2 | 9/2008 | Angel et al. | |
| 7,833,189 B2 | 11/2010 | Hunter et al. | |
| 8,172,790 B2 | 5/2012 | Hunter et al. | |
| 2002/0055729 A1 | 5/2002 | Goll | |
| 2002/0095124 A1 | 7/2002 | Palasis et al. | |
| 2003/0065306 A1 | 4/2003 | Grund et al. | |
| 2004/0010207 A1 | 1/2004 | Flaherty et al. | |
| 2004/0106893 A1 | 6/2004 | Hunter | |
| 2004/0106894 A1 | 6/2004 | Hunter et al. | |
| 2004/0143213 A1 | 7/2004 | Hunter et al. | |
| 2004/0260234 A1* | 12/2004 | Srinivasan et al. | 604/66 |
| 2006/0258986 A1 | 11/2006 | Hunter et al. | |

FOREIGN PATENT DOCUMENTS

| | | |
|---|---|---|
| DE | 101 46 535 A | 4/2003 |
| EP | 0 599 940 B1 | 12/1997 |
| EP | 0 834 330 A2 | 4/1998 |
| EP | 1 020 200 A2 | 7/2000 |
| EP | 1 514 565 A1 | 3/2005 |
| GB | 2307860 A | 6/1997 |
| JP | 2005-87722 | 4/2005 |
| WO | WO 93/03779 A1 | 3/1993 |
| WO | WO 95/07722 A1 | 3/1995 |
| WO | WO 01/37907 A1 | 5/2001 |
| WO | WO 03/039635 A2 | 5/2003 |
| WO | WO 03/068296 A2 | 8/2003 |
| WO | WO 03/086510 A1 | 10/2003 |
| WO | WO 2004/021882 A2 | 3/2004 |
| WO | WO 2004/022138 A2 | 3/2004 |
| WO | WO 2004/071936 A2 | 8/2004 |
| WO | WO 2004/101025 A2 | 11/2004 |
| WO | WO 2004/112871 A1 | 12/2004 |
| WO | WO 2006/086720 A2 | 8/2006 |
| WO | WO 2006/086774 A2 | 8/2006 |
| WO | WO 2008/027579 A1 | 3/2008 |

OTHER PUBLICATIONS

Written Opinion for Int'l Application No. PCT/US2006/004899; Date Mailed: Nov. 17, 2006.
International Preliminary Report of Patentability for Int'l Application No. PCT/US2006/004899; Date Mailed: Aug. 14, 2007.
International Search Report for Int'l Application No. PCT/US2006/005043; Date Mailed: Nov. 16, 2006.
Written Opinion for Int'l Application No. PCT/US2006/005043; Date Mailed: Nov. 16, 2006.
International Preliminary Report of Patentability for Int'l Application No. PCT/US2006/005043; Date Mailed: Aug. 14, 2007.
International Search Report for Int'l Application No. PCT/US2007/019247; Date Mailed: Dec. 4, 2007.
Written Opinion for Int'l Application No. PCT/US2007/019247; Date Mailed: Dec. 4, 2007.
International Preliminary Report of Patentability for Int'l Application No. PCT/US2007/019247; Date Mailed: Mar. 3, 2009.
Notice of Allowance mailed Feb. 2, 2012 for U.S. Appl. No. 12/310,456, filed Jul. 2, 2009.

* cited by examiner

CONTROLLED NEEDLE-FREE TRANSPORT

RELATED APPLICATION(S)

This application is a Divisional of U.S. application Ser. No. 11/354,279, filed Feb. 13, 2006, now U.S. Pat. No. 7,833,189, which is a Continuation-in-Part of U.S. application Ser. No. 11/352,916 filed on Feb. 10, 2006, now abandoned, which claims the benefit of U.S. Provisional Application No. 60/652,483, filed on Feb. 11, 2005. The entire teachings of the above applications are incorporated herein by reference.

BACKGROUND

Injection of a liquid such as a drug into a human patient or an agriculture animal is performed in a number of ways. One of the easiest methods for drug delivery is through the skin, which is the outermost protective layer of the body. It is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue. It extends around 10-20 microns from the skin surface and has no blood supply. Because of the density of this layer of cells, moving compounds across the skin, either into or out of the body, can be very difficult.

The current technology for delivering local pharmaceuticals through the skin includes methods that use needles or other skin piercing devices. Invasive procedures, such as use of needles or lances, effectively overcome the barrier function of the stratum corneum. However, these methods suffer from several major disadvantages: local skin damage, bleeding, and risk of infection at the injection site, and creation of contaminated needles or lances that must be disposed of. Further, when these devices are used to inject drugs in agriculture animals, the needles break off from time to time and remain embedded in the animal. Thus, it would be advantageous to be able to inject small, precise volumes of pharmaceuticals quickly through the skin without the potential of a needle breaking off in the animal.

SUMMARY OF THE INVENTION

Some have proposed using needle-free devices to effectively deliver drugs to a biological body. For example, in some of these proposed devices, pressurized gas is used to expel a drug from a chamber into the body. In another device, a cocked spring is released which then imparts a force on a chamber to expel the drug. In these types of devices, however, the pressure applied to the drug decreases as the gas expands or the spring extends. It is desirable, however, for the injection pressure to remain substantially the same or even increase during the injection period. Examples of needleless injection devices are described in U.S. Pat. No. 6,939,323, entitled "Needleless Injector" and U.S. application Ser. No. 10/657, 734, filed on Sep. 8, 2003 and entitled "Needleless Drug Injection Device" both incorporated herein by reference in their entireties.

Other needle-free injection devices are either controllable in a very limited sense (e.g., gas discharge actuators or spring actuators) or are controllable in a feed-forward sense (e.g., shaped memory materials, such as a nickel-titanium alloy known as Nitinol)—an injection profile being determined a priori and fed forward to a pressure actuator prior to injection.

In accordance with aspects of the invention, a servo-controlled needle-free transfer device transfers a substance across a surface of a biological body. The device includes an actuator capable of generating a high-speed, high-pressure pulse that is both controllable and highly predictable. The device can be combined with a servo-controller receiving inputs from one or more sensors. Beneficially, the transfer device can adjust or tailor the pressure profile of a transfer in real-time. That is, the transfer device can adjust a pressure profile of the transfer during the course of the transfer responsive to a physical property also sensed during the course of the transfer.

The servo-controlled needle-free injector provides for the injection of a formulation into an animal that is dynamically controlled, or tailored in real-time according to requirements of a particular animal and/or other local environmental factors. Such control allows for a single injection device to deliver controlled injection of a formulation responsive to other conditions and requirements by adjusting injection pressure responsive to local thickness of the skin and/or other environmental factors, such as temperature.

In one aspect of the invention, a needle-free, transdermal transfer device includes a reservoir for storing the substance; a nozzle in fluid communication with the reservoir; and a controllable electromagnetic actuator in communication with the reservoir. The electromagnetic actuator includes a stationary magnet assembly providing a magnetic field and a coil assembly slidably disposed with respect to the magnet assembly. The coil assembly receives an electrical input and generates in response a force proportional to the received input. The force results from interaction of an electrical current, induced in the coil assembly by the electrical input, and the magnetic field. The force can be used for needle-free transfer of the substance between the reservoir and the biological body. Thus, a Lorentz force drive transfers a substance, such as fluid, across the surface of the body. The needle-free transfer is also variable, responsive to variations in the received input during the course of an actuation.

Needle-free drug injection apparatus and methods described herein use a specially-configured electromagnetic actuator in combination with one or more nozzles to effectively inject a drug through an animal's skin to a selected depth without first piercing the skin with a lance or needle. The same device can also be used to collect a sample from the animal.

The controllable electromagnetic actuator is bi-directional, being capable of generating a positive force responsive to a first electrical input and a negative force responsive to a second electrical input. The electromagnetic actuator forces the substance through a nozzle, producing a jet having sufficient velocity to pierce the surface of the biological body. For example, in some embodiments, the substance is expelled through the nozzle with an injection velocity of at least about 100 meters per second. The force and nozzle can also be controlled to produce an injection to a desired depth. The electrical input signal can be provided by a rechargeable power source. In some embodiments, the controllable electromagnetic actuator itself is adapted to recharge the rechargeable power source.

The device also includes a controller in electrical communication with the controllable electromagnetic actuator. The device may further include at least one sensor in electrical communication with the controller, the sensor sensing a physical property and the controller generating the electrical input responsive to the sensed physical property. For example, the sensed property may be one or more of position, force, pressure, current, and voltage. The controller may include a processor that contributes to the generation of an electrical input. The device optionally includes an analyzer adapted to analyze a sample collected from the body. The controller can be adapted to provide an electrical input responsive to the analyzed sample.

In some embodiments, a remote communications interface is also provided in electrical communication with the controller. In this configuration, the controller can generate the electrical input responsive to a communication received through the remote communications interface.

The device can be configured as a multi-shot device capable of providing several independent needle-free transfers. Beneficially, these needle-free transfers may occur in rapid succession. This configuration supports treatment of a substantial surface area by administering multiple transfers that are spaced apart across the surface.

The electromagnetic actuator may include a magnet assembly providing a magnetic field. The magnet assembly is generally fixed in position relative to the nozzle. The actuator also includes an electrically conducting coil assembly of at least one turn carrying an electrical current related to the electrical input. The coil assembly is slidably disposed with respect to the magnet assembly. A current produced within the coil assembly interacts with the magnetic field to produce a force responsive to the direction and magnitudes of the electrical current and the magnetic field. Preferably, the magnetic field is radially directed with respect to the coil.

The mechanical force is applied to a reservoir coupled at one end to a nozzle, producing a pressure within the reservoir. The magnitude of the pressure varies according to the mechanical force and causes transfer of a substance across the surface of the biological body between the biological body and the reservoir. Beneficially, the applied force can be bi-directional, producing with the same actuator a positive pressure and a negative pressure or vacuum. Additionally, the applied mechanical force can be varied during the course of an actuation cycle by varying the electrical input.

In some embodiments, the rise-time associated with producing the generated force is about 5 milliseconds or less. The resulting force and stroke provided by the actuator are sufficient in magnitude and duration to transfer a volume of up to at least about 300 micro liters of substance. The compact size and power requirements of the actuator support a portable, hand-held unit including a reservoir, nozzle, power source, and the controllable electrical actuator.

A method of treating a disease using the device includes first piercing a surface of a biological body with a needle-free transdermal transport device. The needle-free device then collects a sample from the biological body by creating a vacuum within the reservoir to suck a sample or bolus from the body into the reservoir. A dosage of an active compound is next determined responsive to the collected sample. The needle-free device injects the determined dosage of active compound into the biological body. For example, a sample of blood is extracted from a patient. The sample is analyzed to determine a blood sugar level. The determined value is then used to calculate a dosage of insulin for the patient, the dosage being administered by controlling the electrical input to the device.

Collecting a sample may include injecting a first substance, such as a saline solution. A sample is then collected and re-injected using the same needle-free device. The sample re-injection process can be repeated multiple times to achieve a suitable bolus of interstitial fluid from the body.

In another aspect of the invention, a linear electromagnetic actuator includes a stationary magnet assembly providing a magnetic field and a coil receiving an electrical input. The coil is slidably disposed with respect to the magnet assembly. The device also includes a bearing that is slidably engaged with at least a portion of the coil. Linear movement of the coil responsive to a force generated by interaction of the electrical input within the coil and the magnetic field is facilitated by the bearing.

Although the invention is described herein in the context of needle-free transfers, one or more of the concepts described herein can also be combined with a needle to accomplish transfer of a substance across the surface of a body, the surface being pierced first by the needle.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

A needle-free transdermal transport device, or injection device, is configured to inject a substance beneath the skin of an animal body. Injection devices include devices having one or more needles configured to pierce the skin prior to injection of the substance (e.g., typical hypodermic needle). Other injection devices are configured to inject a substance beneath the skin without first piercing the skin with a needle (i.e., needle-free). It should be noted that the term "needle-free" as used herein refers to devices that inject without first piercing the skin with a needle or lance. Thus, needle-free devices may include a needle, but the needle is not used to first pierce the skin. Some needle-free injection devices rely on a pioneer projectile ejected from the device to first pierce the skin. Other needle-free injection devices rely on pressure provided by the drug itself.

Figure 1:
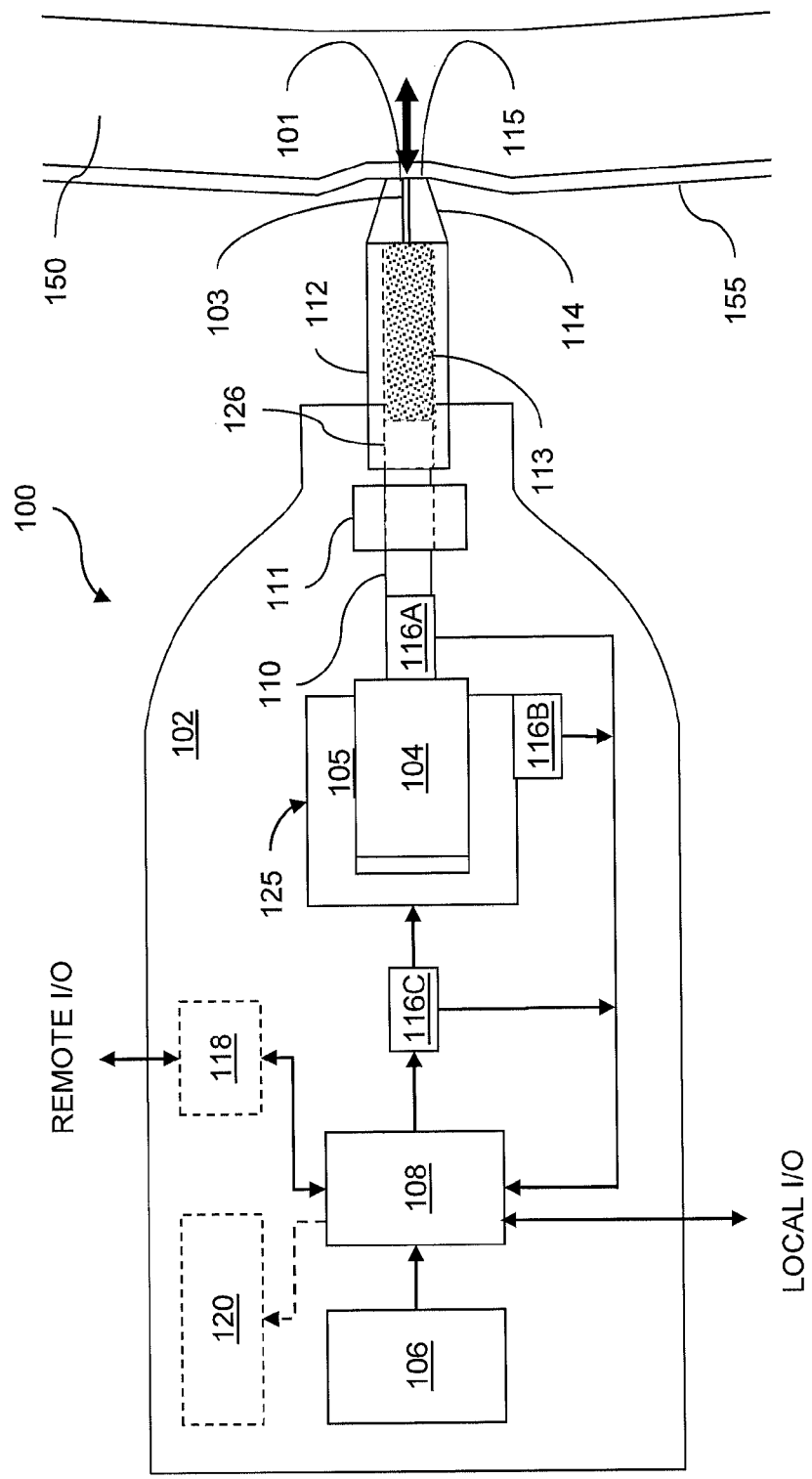
FIG. 1 is a schematic block diagram of one embodiment of a controllable, needle-free transdermal transfer device.

Referring to FIG. 1, there is shown a schematic block diagram of an exemplary needle-free transdermal transport device 100 used to transfer a substance across the surface 155 of a biological body 150. For example, the device 100 can be used to inject a liquid formulation of an active principle, for example, a drug, into biological body such as an agriculture animal or human being. Alternatively or in addition, the same device 100 can be used to collect a sample from a biological body 150 by withdrawing the collected sample through the surface 155 of the body and into an external reservoir 113 that may be provided within the device 100.

The device 100 typically includes a nozzle 114 to convey the substance through the surface 155 of the biological body at the required speed and diameter to penetrate the surface 155 (e.g., skin) as required. Namely, substance ejected from the nozzle 114 forms a jet, the force of the jet determining the depth of penetration. The nozzle 114 generally contains a flat surface, such as the head 115 that can be placed against the skin and an orifice 101. It is the inner diameter of the orifice 101 that controls the diameter of the transferred stream. Additionally, the length of an aperture, or tube 103, defining the orifice 101 also controls the transfer (e.g., injection) pressure.

Preferably, the biological surface 155 is stretched prior to transfer of the substance. First stretching the surface or skin permits the skin to be pierced using a lower force than would otherwise be required. An analogy would be comparing a flaccid balloon to a taught balloon. The flaccid balloon would generally much more difficult to pierce.

Stretching may be accomplished by simply pressing the nozzle 114 into the surface 155 of the skin. In some embodiments, a separate surface reference or force transducer is included to determine when the surface 155 has been sufficiently stretched prior to transfer. Such a sensor can also be coupled to a controller, prohibiting transfer until the preferred surface properties are achieved.

In some embodiments, a standard hypodermic needle is cut to a predetermined length and coupled to the head 115. One end of the needle is flush, or slightly recessed, with respect to the surface of the head 115 that contacts the skin to avoid puncturing the skin during use. The internal diameter of the needle (e.g., 100 µm) defines the diameter of the aperture, and the length of the needle (e.g., 5 mm) together with the aperture dimension controls the resulting injection pressure, for a given applicator pressure. In other embodiments, a hole can be drilled directly into the head 115 to reduce assembly steps. In general, the length of the orifice is selectable, for example ranging from 500 µm to 5 mm, while its diameter can range from 50 µm to 200 µm. In one particular embodiment, the diameter of the orifice is about 120 µm.

The nozzle 114 can be coupled to a syringe 112 defining a reservoir 113 for temporarily storing the transferred substance. The syringe 112 also includes a plunger or piston 126 having at least a distal end slidably disposed within the reservoir 113. Movement of the plunger 126 along the longitudinal axis of the syringe 112 in either direction creates a corresponding pressure within the reservoir 113. In some embodiments, the syringe 112 is integral to the device 100. In other embodiments, the syringe 112 is separately attachable to the device 100. For example, a commercially-available needle-free syringe 112 can be attached to the device 100, such as a model reference no. 100100 syringe 112 available from Equidine Systems Inc. of San Diego, Calif.

The nozzle 114 can be releasably coupled to the syringe 112 or the distal end of the device 100, such that different nozzles can be used for injecting and sampling (i.e., sucking), each different nozzle tailored for its intended use. Thus, a sampling nozzle may include a larger orifice 101, tapering into the lumen 103 thereby promoting a more efficient collection, or greater capacity sample.

Beneficially, a pressure is selectively applied to the chamber 113 using a controllable actuator. A specially-designed electromagnetic actuator 125 is configured to generate a high-pressure pulse having a rapid rise time (e.g., less than 1 millisecond). The actuator 125 can be used in needle-free injection devices that rely on high-pressure actuators to inject a formulation beneath the skin. Beneficially, the actuator is dynamically controllable, allowing for adjustments to the pressure-versus-time during actuation. At least one advantage of the electromagnetic actuator over other needle-free devices is its relatively quiet operation. Actuation involves movement of a freely suspended coil within a gap, rather than the sudden release of a spring or the discharge of a gas. Actuation of the freely-moving coil in the manner described herein results in quiet operation, which is an important feature as it contributes to reducing pain and anxiety during administration to the recipient and to others that may be nearby.

In more detail, the electromagnetic actuator 125 is configured to provide a linear force applied to the plunger 126 to achieve transdermal transfer of the substance. Transfer of the force can be accomplished with a force-transfer member 110, such as a rigid rod slidably coupled through a bearing 111. The rod may be secured at either end such that movement of the actuator in either direction also moves the plunger 126. The bearing restricts radial movement of the rod 110, while allowing axial movement.

In some embodiments, the actuator 125 includes a stationary component, such as a magnet assembly 105, and a moveable component, such as coil assembly 104. A force produced within the coil assembly 104 can be applied to the plunger 126 either directly, or indirectly through the rod 110 to achieve transdermal transfer of the substance. Generally, the actuator 125, bearing 111 and syringe 112 are coupled to a frame or housing 102 that provides support and maintains fixed position of these elements during an actuation.

In some embodiments, the device 100 includes a user interface 120 that provides a status of the device. The user interface may provide a simple indication that the device is ready for an actuation. For example, a light emitting diode (LED) coupled to a controller 108 can be enabled when sufficient conditions are satisfied for an injection. More elaborate user interfaces 120 can be included to provide more detailed information, including a liquid crystal display (LCD), cathode ray tube (CRD), charge-coupled device (CCD), or any other suitable technology capable of conveying detailed information between a user and the device 100. Thus, user interface 120 may also contain provisions, such as a touch screen to enable an operator to provide inputs as user selections for one or more parameters. Thus, a user may identify parameters related to dose, sample, parameters related to the biological body, such as age, weight, etc.

A power source 106 provides an electrical input to the coil assembly 104 of the actuator 125. As will be described in more detail below, an electrical current applied to the coil assembly 104 in the presence of a magnetic field provided by the magnet assembly 105 will result in a generation of a mechanical force capable of moving the coil assembly 104 and exerting work on the plunger 126 of the syringe 112. The electromagnetic actuator is an efficient force transducer supporting its portability. An exemplary device described in more detail below expends about 50 Joules of energy to deliver about 200 micro-liters of a fluid. For comparison, a standard 9-volt batter can provide up to about 8,500 Joules.

A controller 108 is electrically coupled between the power source 106 and the actuator 125, such that the controller 108 can selectively apply, withdraw and otherwise adjust the electrical input signal provided by the power source 106 to the actuator 125. The controller 108 can be a simple switch that is operable by a local interface. For example, a button provided on the housing 102 may be manipulated by a user, selectively applying and removing an electrical input from the power source 106 to the actuator 125. In some embodiments, the controller 108 includes control elements, such as electrical circuits, that are adapted to selectively apply electrical power from the power source 106 to the actuator 125, the electrical input being shaped by the selected application. Thus, for embodiments in which the power source 106 is a simple battery providing a substantially constant or direct current (D.C.) value, can be shaped by the controller to provide a different or even time varying electrical value. In some embodiments, the controller 108 includes an on-board microprocessor, or alternatively an interconnected processor or personal computer providing multifunction capabilities.

In some embodiments, the needle-free transdermal transport device 100 includes a remote interface 118. The remote interface 118 can be used to transmit information, such as the status of the device 100 or of a substance contained therein to a remote source, such as a hospital computer or a drug manufacturer's database. Alternatively or in addition, the remote interface 118 is in electrical communication with the controller 108 and can be used to forward inputs received from a remote source to the controller 108 to affect control of the actuator 125.

The remote interface 118 can include a network interface, such as a local area network interface (e.g., Ethernet). Thus, using a network interface card, the device 100 can be remotely accessed by another device or user, using a personal computer also connected to the local area network. Alternatively or in addition, the remote interface 118 may include a wide-area network interface. Thus, the device 100 can be remotely accessed by another device or user over a wide-area network, such as the World-Wide Web. In some embodiments, the remote interface 118 includes a modem capable of interfacing with a remote device/user over a public-switched telephone network. In yet other embodiments, the remote interface 118 includes a wireless interface to access a remote device/user wirelessly. The wireless interface 118 may use a standard wireless interface, such as Wi-Fi standards for wireless local area networks (WLAN) based on the IEEE 802.11 specifications; new standards beyond the 802.11 specifications, such as 802.16 (WiMAX); and other wireless interfaces that include a set of high-level communication protocols such as ZigBee, designed to use small, low power digital radios based on the IEEE 802.15.4 standard for wireless personal area networks (WPANs).

In some embodiments the controller receives inputs from one or more sensors adapted to sense a respective physical property. For example, the device 100 includes a transducer, such as a position sensor 116B used to indicate location of an object's coordinates (e.g., the coil's position) with respect to a selected reference. Similarly, a displacement may be used to indicate movement from one position to another for a specific distance. Beneficially, the sensed parameter can be used as an indication of the plunger's position as an indication of dose. In some embodiments, a proximity sensor may also be used to indicate a portion of the device, such as the coil, has reached a critical distance. This may be accomplished by sensing the position of the plunger 126, the force-transfer member 110, or the coil assembly 104 of the electromagnetic actuator 125. For example, an optical sensor such as an optical encoder can be used to count turns of the coil to determine the coil's position. Other types of sensors suitable for measuring position or displacement include inductive transducers, resistive sliding-contact transducers, photodiodes, and linear-variable-displacement-transformers (LVDT).

Other sensors, such as a force transducer 116A can be used to sense the force applied to the plunger 126 by the actuator 125. As shown, a force transducer 116A can be positioned between the distal end of the coil assembly and the force transfer member 110, the transducer 116A sensing force applied by the actuator 125 onto the force-transfer member 110. As this member 110 is rigid, the force is directly transferred to the plunger 126. The force tends to move the plunger 126 resulting in the generation of a corresponding pressure within the reservoir 113. A positive force pushing the plunger 126 into the reservoir 113 creates a positive pressure tending to force a substance within the reservoir 113 out through the nozzle 114. A negative force pulling the plunger 126 proximally away from the nozzle 114 creates a negative pressure or vacuum tending to suck a substance from outside the device through the nozzle 114 into the reservoir 113. The substance may also be obtained from an ampoule, the negative pressure being used to pre-fill the reservoir 113 with the substance. Alternatively or in addition, the substance may come from the biological body representing a sampling of blood, tissue, and or other interstitial fluids. In some embodiments, a pressure transducer (not shown) can also be provided to directly sense the pressure applied to a substance within the chamber.

An electrical sensor 116C may also be provided to sense an electrical input provided to the actuator 125. The electrical may sense one or more of coil voltage and coil current. The sensors 116A, 116B, 116C (generally 116) are coupled to the controller 108 providing the controller 108 with the sensed properties. The controller 108 may use one or more of the sensed properties to control application of an electrical input from the power source 106 to the actuator 125, thereby controlling pressure generated within the syringe 112 to produce a desired transfer performance. For example, a position sensor can be used to servo-control the actuator 125 to pre-position the coil assembly 104 at a desired location and to stabilize the coil 104 once positioned, and conclude an actuation cycle. Thus, movement of the coil assembly 104 from a first position to a second position corresponds to transfer of a corresponding volume of substance. The controller can include a processor programmed to calculate the volume based on position give the physical size of the reservoir.

An actuation cycle described in more detail below, generally correspond to initiation of an electrical input to the actuator 125 to induce transfer of a substance and conclusion of the electrical input to halt transfer of the substance. A servo-control capability combined with the dynamically controllable electromagnetic actuator 125 enables adjustment of the pressure during the course of an actuation cycle. One or more of the sensors 116 can be used to further control the actuation cycle during the course of the transfer, or cycle. Alternatively or in addition, one or more of local and remote interfaces can also be used to further affect control of the actuation cycle.

In some implementations, the controller 108 is coupled with one more other sensors (not shown) that detect respective physical properties of the biological surface. This information can be used to servo-control the actuator 125 to tailor the injection pressure, and, therefore, the depth of penetration of drug into the skin for a particular application. For instance, when the device 100 is used on a baby, the sensor detects the softness of the baby's skin, and the controller 108 uses the properties of the baby's skin and consequently reduces the injection pressure. The injection pressure can be adjusted, for example, by controlling the electrical input signal applied to the actuator 125 and/or the current pulse rise time and/or duration. When used on an adult or someone with sun-damaged skin, the controller may increase the injection pressure. The injection pressure may be adjusted depending on location of the skin on the body, for example, the face versus the arm of the patient. The injection pressure can also be tailored to deliver the drug just underneath the skin or deep into muscle tissue. Moreover, the injection pressure may be varied over time. For instance, in some implementations, a large injection pressure is initially used to pierce the skin with the drug, and then a lower injection pressure is used to deliver the drug. A larger injection may also be used to break a seal that seals the chamber or vial.

In more detail, the power source 106 can be external to the device 100. For example, the device 100 can be coupled to a separate electrical power supply. Preferably, however, the power source 106 is self-contained within the device 100 to promote portability of the device 100. Such portability is particularly beneficial in field applications, such as treating livestock or administrating of medicines, such as vaccines to people or animals in remote areas.

The power source 106 can include a replaceable battery, such as a ubiquitous 9-volt dry cell battery. Alternatively, the power source 106 includes a rechargeable device, such as a rechargeable battery (e.g., gel batteries; lead-acid batteries; Nickel-cadmium batteries; Nickel metal hydride batteries; Lithium ion batteries; and Lithium polymer batteries). In some embodiments, the power source 106 includes a storage capacitor. For example, a bank of capacitors can be charged through another power source, such as an external electrical power source.

In more detail, the electromagnetic actuator 125 includes a conducting coil assembly 104 disposed relative to a magnetic field, such that an electrical current induced within the coil results in the generation of a corresponding mechanical force. The configuration is similar, at least in principle, to that found in a voice coil assembly of a loud speaker. Namely, the relationship between the magnetic field, the electrical current and the resulting force is well defined and generally referred to as the Lorentz force law.

Preferably, the coil 104 is positioned relative to a magnetic field, such that the magnetic field is directed substantially perpendicular to the direction of one or more turns of the coil 104. Thus, a current induced within the coil 104 in the presence of the magnetic field results in the generation of a proportional force directed perpendicular to both the magnetic field and the coil (a relationship referred to as the "right hand rule").

Figure 2A:
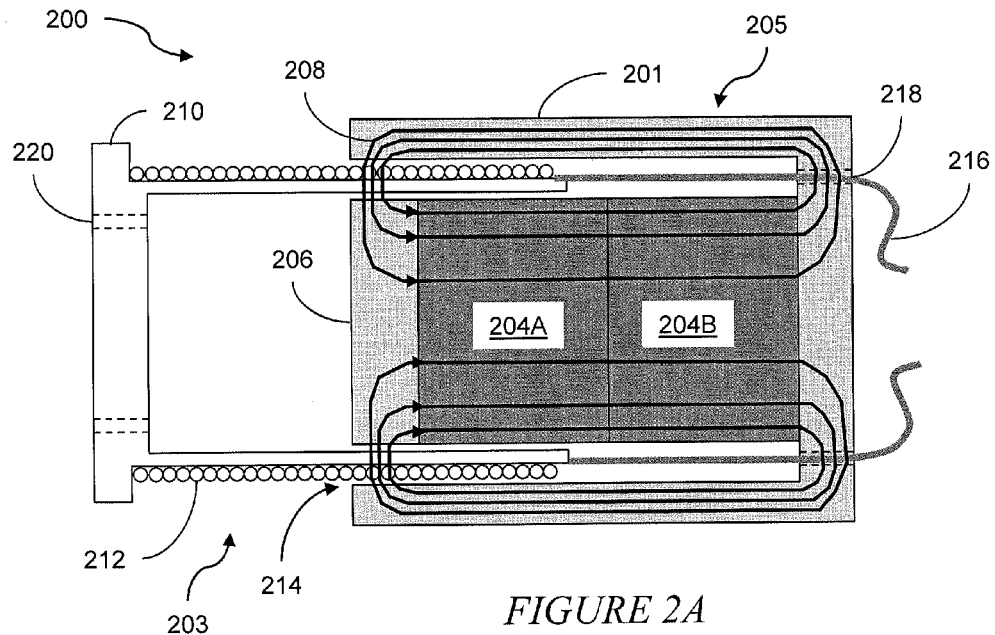
FIGS. 2A and 2B are cross-sectional diagrams of one embodiment of a controllable electromagnetic actuator usable with the device of FIG. 1, respectively shown in an extended and retracted configuration.
Figure 2B:
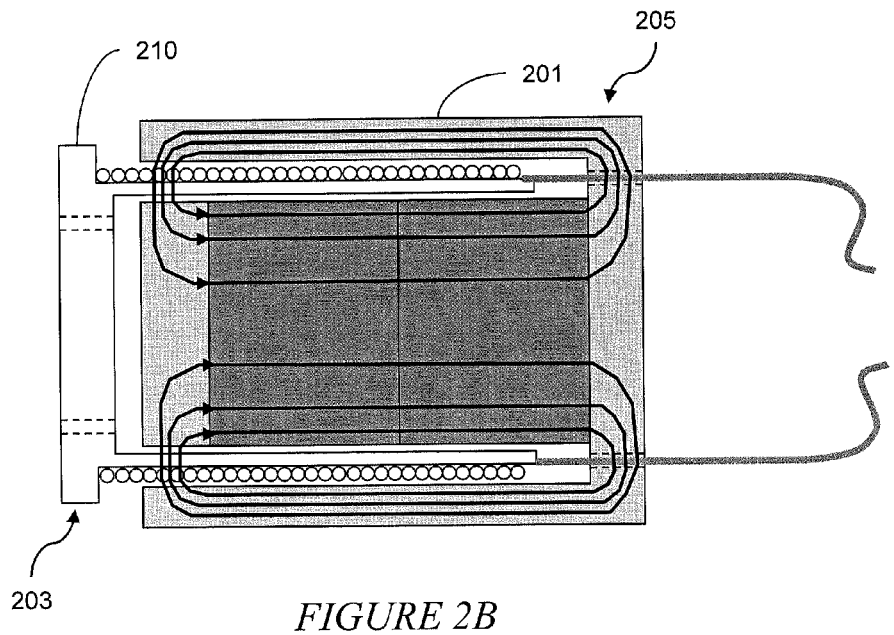

In more detail a cross-sectional diagram of an electromagnetic impulse actuator 200 is shown in FIG. 2A. The device 200 includes a magnet assembly 205 defining an annular slotted cavity 214 and a coil assembly 203 slidably disposed therein. The stroke of the coil 212 can be controlled by the lengths of the coil and magnet assembly. Thus, the electromagnetic actuator can be configured to transfer a substantial volume of a substance during a single, sustained stroke. For example, a volume of up to 300 micro-liters or more may be transferred with a single stroke. Alternatively or in addition, the entire contents of a vial or syringe may be transferred in multiple smaller doses. For example, substantially the entire contents of a 300 micro-liter vial may be transferred to an animal in ten separate injections of 30 micro-liters each.

The controllability of the actuator also allows for a precise transfer. For example, a substance may be delivered to a biological body with minimum volumetric increments of about 1%. Thus, for a 200 micro-liter volume, the dosage may be tailored in 200 nano-liter steps. Thus, a single syringe loaded with a sufficient volume can deliver various doses by controlling the electrical input to the coil. Operation of such an actuator is deterministic further lending itself to precision control.

The magnet assembly 205 includes a column of magnets 204A, 204B disposed along a central axis. The column of magnets can be created by stacking one or more magnetic devices. For example, the magnetic devices can be permanent magnets. As a greater magnetic field will produce a greater mechanical force in the same coil, thus stronger magnets are preferred. As portability and ease of manipulation are important features for a hand-held device 100, high-density magnets are preferred.

One such category of magnets are referred to as rare-earth magnets, also know as Neodymium-Iron-Boron magnets (e.g., $Nd_2Fe_{14}B$). Magnets in this family are very strong in comparison to their mass. Currently available devices are graded in strength from about N24 to about N54—the number after the N representing the magnetic energy product, in megagauss-oersteds (MGOe). In one particular embodiment, N50 magnets are used. The magnetic field produced by the magnets generally follows field lines 208, with rotational symmetry about the central axis for the configuration shown.

The magnets 204A, 204B are attached at one end of a right-circular cylindrical shell 201 defining a hollowed axial cavity and closed at one end. An annular slot remains being formed between the magnets 204A, 204B and the interior walls of the case and accessible from the other end of the shell 201. An exemplary shell 201 is formed with an outside diameter of about 40 mm and an inside diameter of about 31.6 mm, resulting in a wall thickness of about 4.2 mm. In this embodiment, the magnets 204A, 204B are cylindrical, having a diameter of about 25.4 mm.

The shell 201 is preferably formed from a material adapted to promote containment therein of the magnetic fields produced by the magnets 204A, 204B. For example, the shell 201 can be formed from a ferromagnetic material or a ferrite. One such ferromagnetic material includes an alloy referred to as carbon steel (e.g., American Iron and Steel Institute (AISI) 1026 carbon steel). An end cap 206 is also provided of similar ferromagnetic material being attached to the other end of the magnets 204A, 204B. Placement of the end cap 206 acts to contain the magnetic field therein and promoting a radially-directed magnetic field between the annular gap formed between the end cap 206 and the outer walls of the shell 201. The end cap is generally thicker than the shell walls to promote containment of the magnetic fields as they loop into the end of the top magnet 204A. For the exemplary shell 201 embodiment described above, the end cap 206 has an axial thickness of about 8 mm.

The coil assembly 203 includes a coil 212 formed from a conducting material, such as copper wire wound about a bobbin 210. The bobbin 210 can be cylindrical and defines an axial cavity sized to fit together with the coil 212 within the annular cavity 214. In some embodiments, the bobbin 210 is substantially closed at the end juxtaposed to the annular cavity 214. The closed end forms a force-bearing surface adapted to push against a plunger 126 (FIG. 1) or force-bearing rod 110 (FIG. 1).

A strong, yet light-weight coil assembly 203 is preferred for applications requiring a rapid generation of substantial force, such as needle-free transfers. Preferably, the bobbin is formed from a strong, yet light-weight material such as aluminum or epoxy-loaded fiberglass. One such family of glass reinforced epoxy is sold under the trade name GAROLITE®. Suitable material selected from this family includes G10/FR4 material offering extremely high mechanical strength, good dielectric loss properties, and good electric strength properties, both wet and dry. Other materials include an all-polymeric reinforced, dull gold colored polytetrafluoroethylene (PTFE) compound that operates exceptionally well against soft mating surfaces such as 316 stainless steel, aluminum, mild steel, brass and other plastics available from Professional Plastics of Fullerton Calif. under the trade name RULON®. The bobbin 210 is thin-walled to fit within the annular slot. The bobbin 210 should also present a low coefficient of friction to those surfaces that may come in contact with either the shell 201, the magnets 204A, 204B or the end cap 206. In some embodiments, a low-friction coating can be applied to the bobbin. Such coatings include fluorocarbons, such as PTFE.

Generally, a non-conducting material such as epoxy-loaded fiberglass is preferred over a conducting material such as aluminum. Eddy currents created in the conducting material as it moves through the magnetic field tend to create a mechanical force opposing motion of the bobbin. Such an opposing force would counteract intentional movement of the coil thereby resulting in an inefficiency. Dielectric materials reduce or eliminate the production of such eddy currents.

A thin-walled bobbin 210 allows for a narrower annular slot 214 thereby promoting a greater magnetic field intensity across the gap. A substantial current flowing within the coil 212 can result in the generation of a substantial thermal load that could result in structural damage (e.g., melting). Other light-weight materials include machinable poly-acetals, which are particularly well suited to high-temperature applications.

Continuing with the exemplary embodiment, the bobbin 210 has an outside diameter of about 27 mm, an internal diameter of about 26 mm, and an axial length of about 46 mm. The coil 212 consists of six layers of 28 gauge copper wire wound onto the bobbin 210 at a rate of about 115 windings per coil length (about 35 mm) resulting in about 700 turns total. Using the N50 magnets with the 1026 carbon steel, the end cap 206 contains between about 0.63 and 0.55 Tesla (the value reducing outwardly along a radius measured from the center of the end cap 206).

Thus, a current flowing through the coil 212 is positioned at right angles to the magnetic field 208 produced between the end cap 206 and the shell 201 wall. This results in the generation of a force on the coil directed along the longitudinal axis, the direction of the force depending upon the directional flow of the current. For the above exemplary device, an electrical input, or drive voltage of about 100 volts applied across the coil for a duration of about 1 millisecond representing the pierce phase of an actuation cycle. A lesser electrical input of about −2 volts is applied for the transfer phase. The polarity of the applied input suggests that the transfer phase is a sample phase collecting a sample from the biological body.

Generally, the coil 212 receives the electrical input signal through two electrical leads 216. The shell 201 includes one or more apertures 218 through which the leads 216 are routed to the power source 106 (FIG. 1). The closed end of the shell 201 may contain one or more additional apertures through which air may be transferred during movement of the coil. Without such apertures and given the relative tight tolerances of the gap between the coil 212 and the annular slot 214, a pressure would build up to oppose movement of the coil. Alternatively or in addition, the bobbin 210 may also have one or more apertures 220 to further inhibit the build up of damping pressures during actuation.

FIG. 2A shows the coil assembly 203 after or during an injection phase in which the coil is forced out of the shell 201 thereby advancing the front plate. FIG. 2B shows the coil assembly 203 retracted within the shell 201 after a sampling phase in which the coil assembly 203 is drawn into the shell 201.

In some embodiments, the conductive coil is configured to carry a relatively high-amplitude electrical current to produce a substantial force resulting in the generation of a substantial pressure. The coil also provides a relatively low inductance to support high-frequency operation thereby enabling rapid rise time (i.e., impulse) response. In some embodiments, the coil provides an inductance of less than 100 millihenries. Preferably, the coil inductance is less than about 50 millihenries. More preferably, the coil inductance is less than about 10 millihenries. For example, the coil inductance can be between about 5 and 10 millihenries. One way of providing the high-current capacity with the low inductance is using a coil formed by a large-diameter conductor that is configured with a low number of turns (e.g., 1 to 3 turns).

The result is a pressure actuator capable of generating a high-pressure pulse with a rapid rise time. Additionally, operation of the actuator is both controllable and highly predictable given the physical properties of the actuator and the input electrical current. Still further, the actuator is reversible providing forces in opposing directions based on the direction of current flow within the coil.

Additionally, the controllability allows for a tailored injection profile that can include a rapid high-pressure pulse to breach the outer layers of skin, followed by a lower-pressure, prolonged pulse to deliver the formulation. Referring to FIG. 3A, an exemplary time varying electrical input is shown. The curve represents variation in an electrical current applied to the coil assembly 104 of the actuator 125. At a first instant of time $t_0$ an electrical current is applied to the coil 104. The current rises from a rest value (e.g., zero amps) to a maximum value $I_P$ remaining at this maximum for a selectable duration and then transitioning to a different current value $I_T$ at a later time $t_1$. The current amplitude may remain substantially at this value, or continue to vary with time until a later time $t_2$, at which the current returns to a rest value.

The entire period of time defined between times $t_2$ and $t_0$ can be referred to as an actuation period, or actuation cycle. For a current input having a shape similar to that just described, the period defined between times $t_1$ and $t_0$ can be referred to as a piercing phase. As the name suggests, the high current value $I_P$ induces a corresponding high pressure that can be used to pierce the surface of a biological body without using a needle or lance. The remainder of the actuation cycle defined between times $t_2$ and $t_1$ can be referred to as a transfer phase. As this name suggests, the relatively lower current value $I_T$ induces a lesser pressure that can be used to transfer a substance from the reservoir 113 (FIG. 1) to the biological body through the perforation in the surface created during the piercing phase.

Figure 3A:
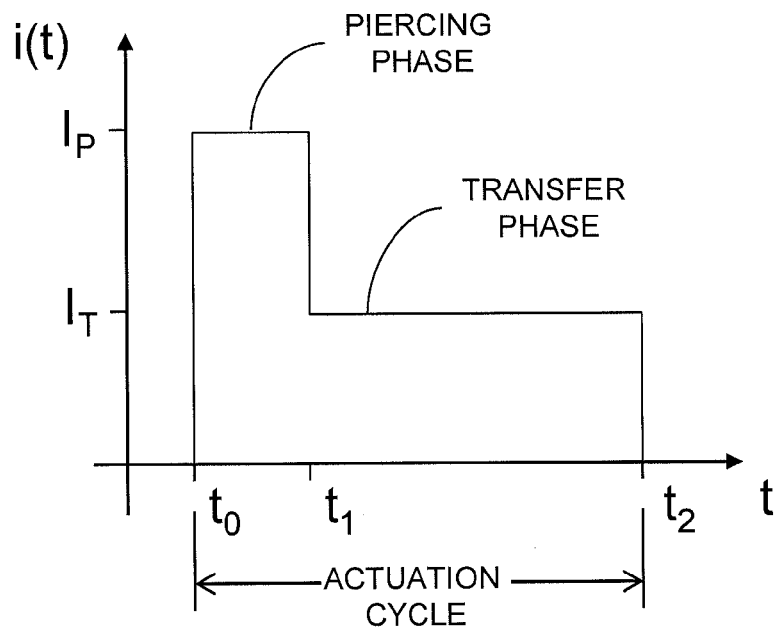
FIG. 3A is a graph depicting a current-versus-time profile of an exemplary electrical input to the controllable electromagnetic actuator of FIG. 2A.
Figure 3B:
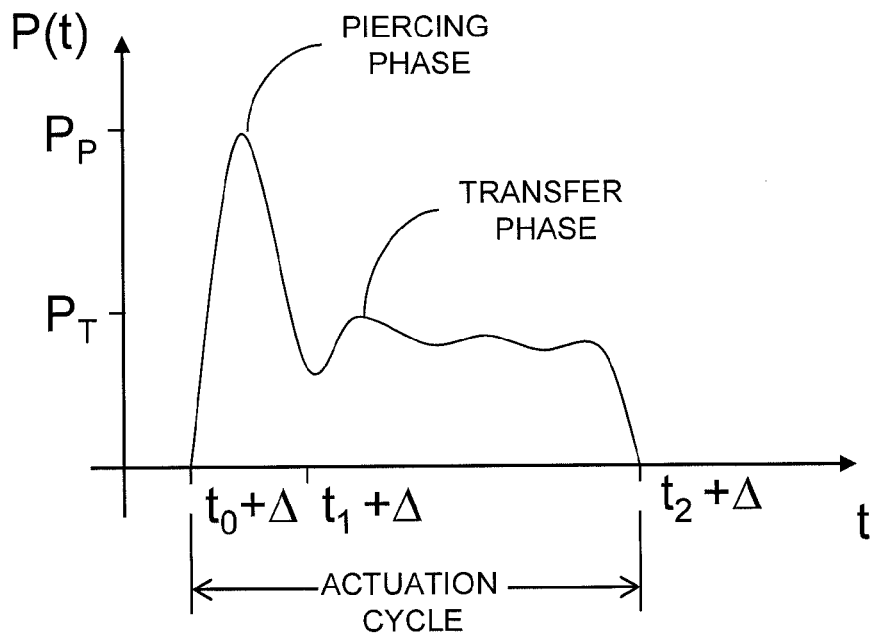
FIG. 3B is a graph depicting a pressure-versus-time profile of an exemplary pressure generated within a reservoir used in the transfer of a substance, the pressure being generated by the controllable electromagnetic actuator responsive to the electrical input of FIG. 3A.

An exemplary plot of a pressure induced within the reservoir 113 (FIG. 1) in response to the electrical input is illustrated in FIG. 3B. As shown, the pressure rises from an initial rest value to a relative maximum value, $P_P$, at a time $t_0$, perhaps with a slight delay $\Delta$ resulting from the transfer characteristics of the electrical coil. This pressure value can be used to create a jet as described above in relation to FIG. 1. As the current is reduced during the transfer phase, the pressure similarly reduces to a lesser value $P_T$ determined to achieve a desired transfer of the substance. The transfer phase continues until a desired volume of the substance is transferred, then the pressure is removed concluding the actuation cycle.

A servo-controlled injector includes a specially-designed electromagnetic pressure actuator configured in combination with a servo controller to generate an injection pressure responsive in real-time to one or more physical properties (e.g., pressure, position, volume, etc.). In some embodiments, the servo-controlled injector is a needle-free device. The electromagnetic pressure actuator generates a high-pressure pulse having a rapid rise time (e.g., less than 1 millisecond) for injecting a formulation beneath the skin. With such a rapid rise time, an entire transfer can be completed in less than about 10 milliseconds. The pressure provided by the actuator can be varied during the actuation of a single injection to achieve a desired result. For example, a first high-pressure is initially provided to the formulation to penetrate the outer surface layer of an animal's skin. Once the skin is penetrated, the pressure is reduced to a second, lower pressure for the remainder of the injection. The servo-controller can be used to determine when the skin is penetrated by sensing a change in pressure within the chamber and to adjust the injection pressure accordingly.

A servo-controller 108 receives input signals from the one or more sensors 116 and generates an output signal according to a predetermined relationship. The servo-controller output can be used to control the pressure by controlling the amplitude of electrical current driving the controllable actuator.

Real-time control can be accomplished by the servo controller 108 repeatedly receiving inputs from the sensors 116, processing the inputs according to the predetermined relationship and generating corresponding outputs. In order to adjust the injection pressure during the course of an injection, the entire sense-control process must be performed numerous times during the period of the injection. For example, a servo-controller 108 can include a high-speed microprocessor capable of processing signals received from the sensors and rapidly providing corresponding output signals at a rate of 100 kHz (i.e., every 10 microseconds). Such rapid response times provide hundreds of opportunities to adjust pressure during the course of a single 5 to 10 millisecond injection.

As friction or drag on the coil assembly 104 represents an inefficiency, the coil can be floating within a cavity of the magnet assembly 105. That is, there is the coil assembly 104 floats within a gap and is allowed to move freely. With no current applied to the coil assembly 104, it would be allowed to slide back and forth with movement of the device 100. Such movement may be undesirable as it may result in unintentional spillage of a substance form the reservoir or introduction of a substance, such as air, into the reservoir. Using a servo-controller with the position sensor 116B, the position of the coil 104 can be adjusted such that the coil 104 is held in place in the presence of external forces (e.g., gravity) by the application of equal and opposite forces induced from the electrical input signal applied to the coil assembly 104.

Alternatively or in addition, the actuator can be coupled to a bellows forming a chamber containing a formulation. For either configuration, actuation results in the generation of a pressure within the chamber, the chamber forcing the formulation through a nozzle.

Figure 4:
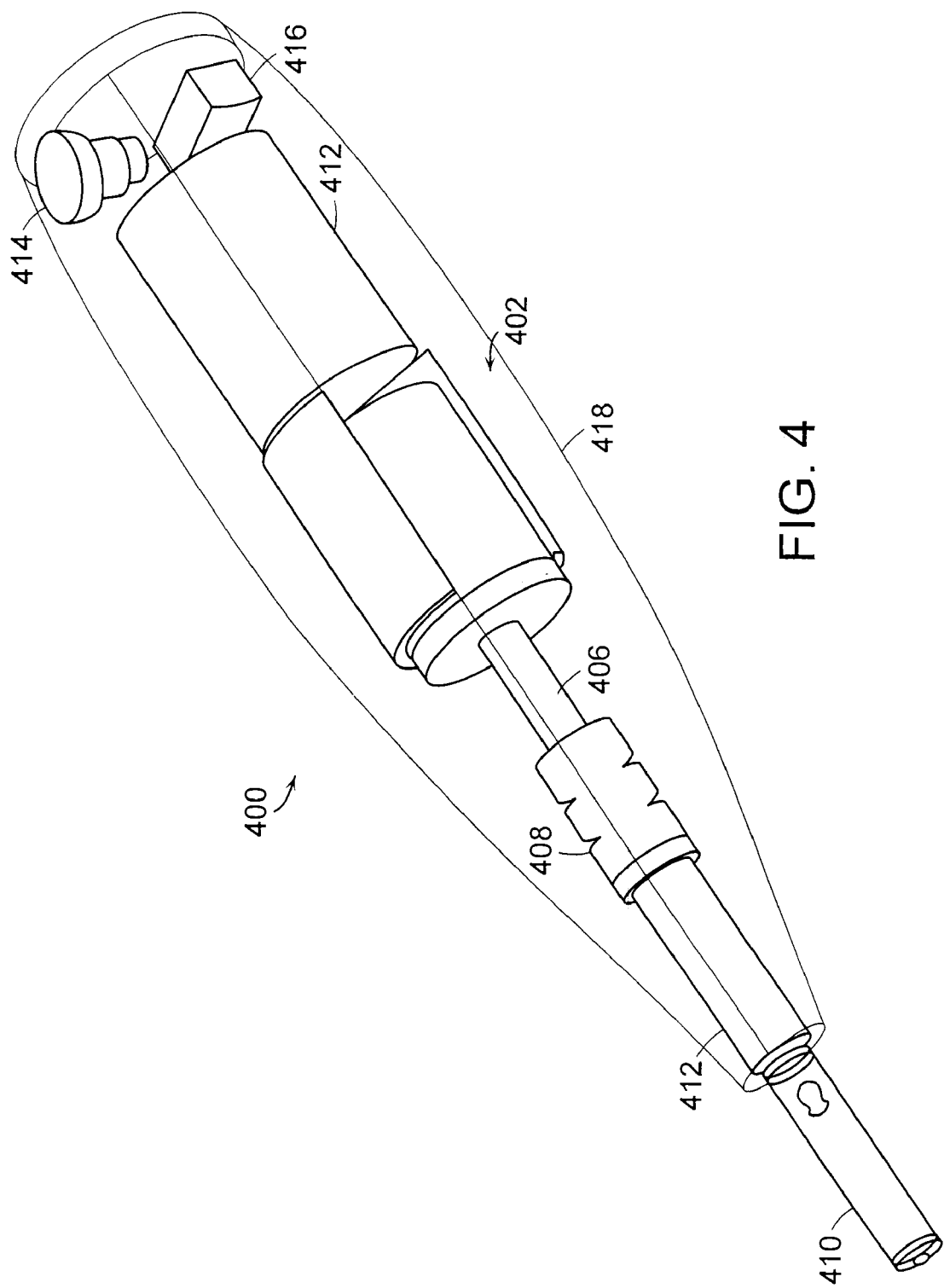
FIG. 4 is a partial cut-away perspective diagram of an embodiment of a controllable needle-free transdermal transfer device.

An exemplary embodiment of a dynamically-controllable needle-free injection device 400 is shown in FIG. 4. The device 400 includes a controllable electromagnetic actuator 402 abutting one end to a pusher rod 406. The axis of the pusher rod 406 is collinear with the longitudinal axis of the actuator 402 and slides through a bearing 408 to inhibit radial movement. A mounting adapter 412 is provided at a distal end of the device 400 for mounting a syringe 410. A plunger of the syringe (not shown) resides within the mounting adapter 412 abutting the other end of the pusher rod 406. A power source, such as a rechargeable capacitor 412 is disposed proximal to the actuator 402 for inducing currents within the actuator 402. The device 400 also includes a button to initiate an injection and a controller 416 to control application of the power source to the actuator 402. A housing, such as an elongated molded plastic case 418 is also provided to secure the different components with respect to each other.

Figure 5:
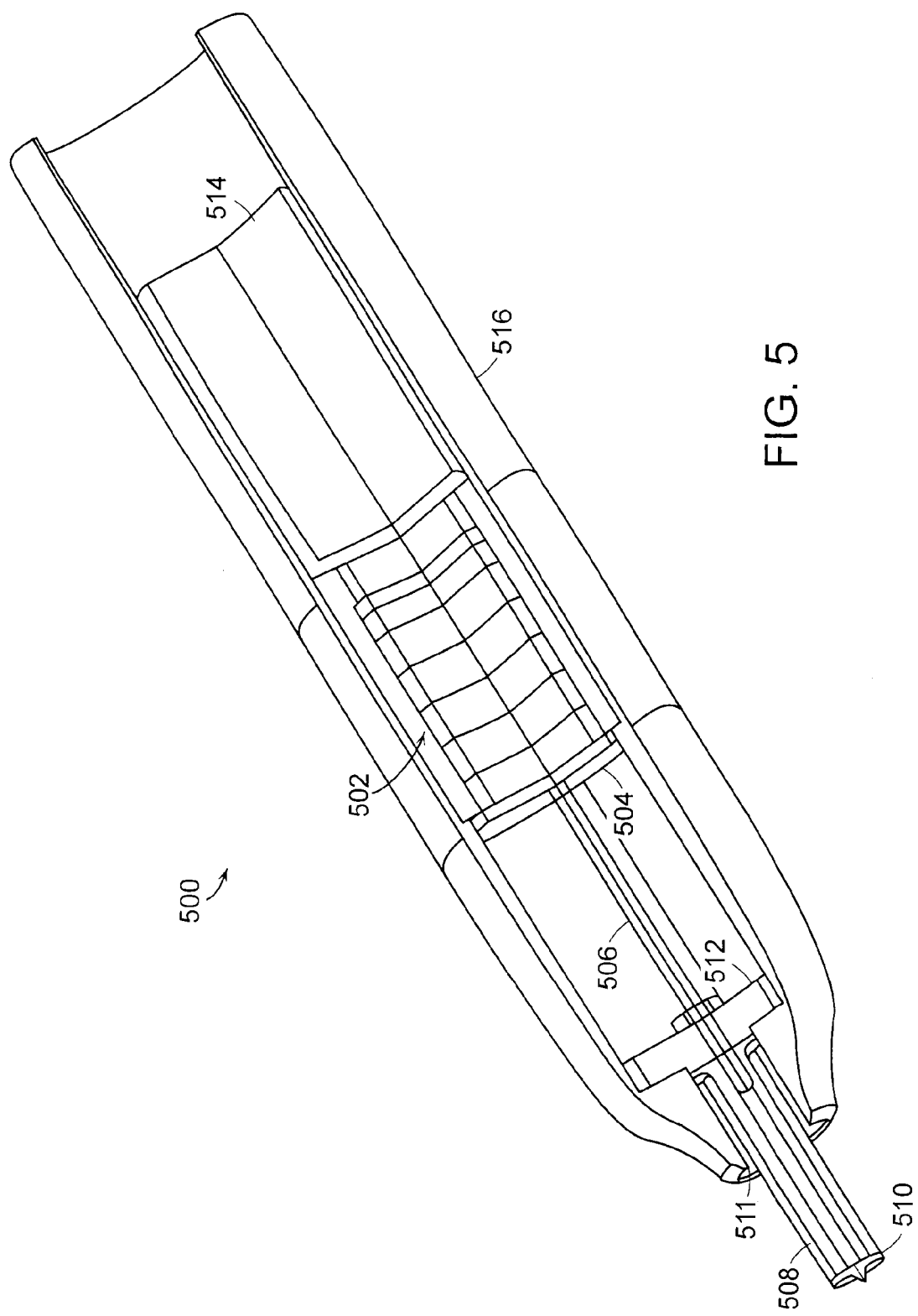
FIG. 5 is a partial cut-away perspective diagram of an alternative embodiment of a controllable needle-free transdermal transfer device.

An exemplary embodiment of a smaller, dynamically-controllable needle-free injection device 500 is shown in FIG. 5. The device 500 includes a compact electromagnetic actuator 502 having a distal force plate 504 adapted to abut a proximal end of a plunger 506 of a syringe 508. The device 500 also includes a mounting member 512 to which a proximal end of the syringe 508 is coupled. A power source 514 is also disposed proximal to the actuator 502, the different components being secured with respect to each other within a housing 516. In some embodiments, a coupler 525 is provided to removably fasten the plunger 528 to the coil assembly 505. This ensures that the plunger is moved in either direction responsive to movement of the coil assembly 505.

Figure 6:
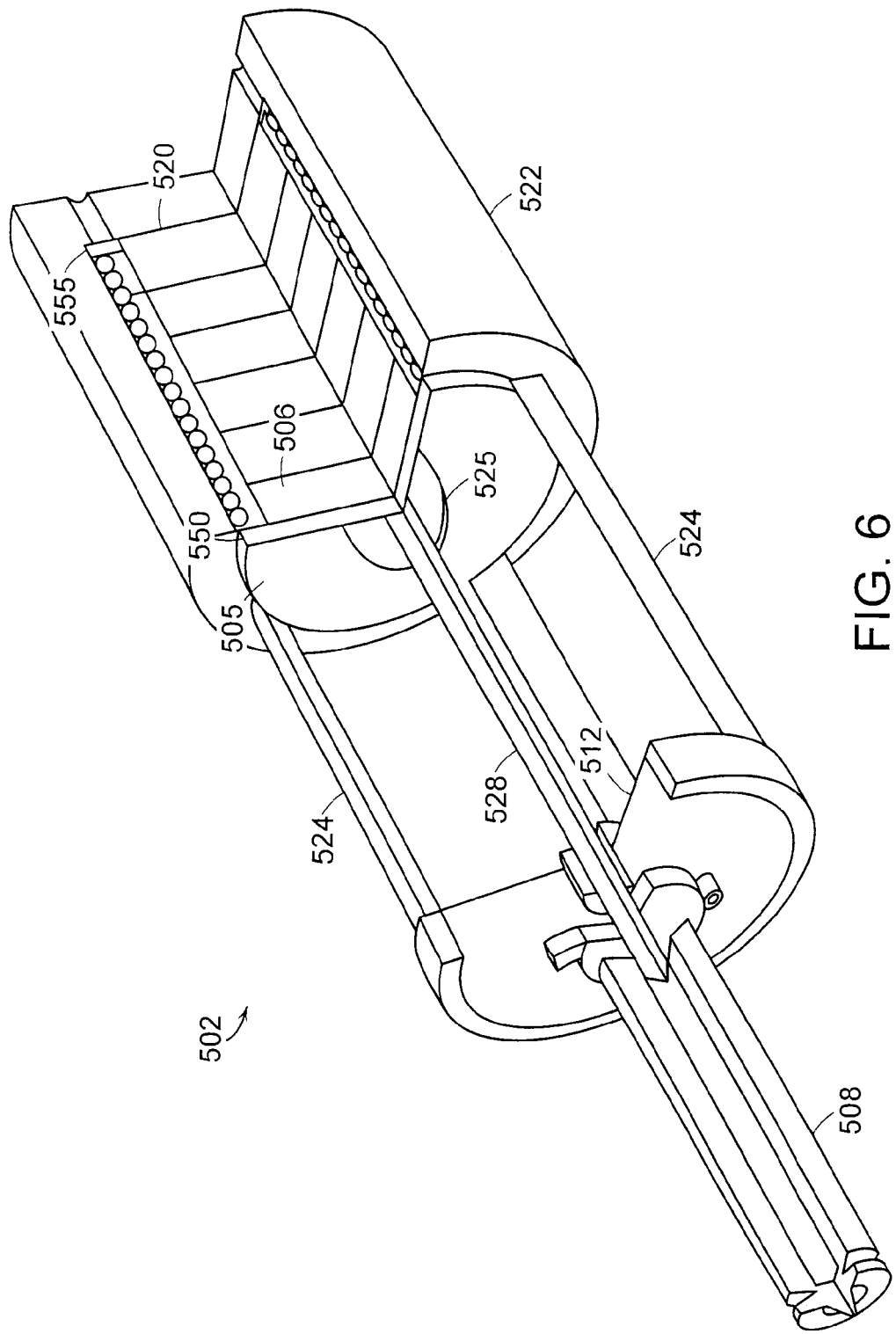
FIG. 6 is a more detailed partial cut-away perspective diagram of the controllable electromagnetic actuator provided in the device of FIG. 5 coupled to a syringe.

Referring to FIG. 6, in more detail, the compact controllable electromagnetic actuator 502 includes a ferromagnetic shell 522 including a central magnetic core 520 capped by a ferromagnetic end cap 506. A coil assembly 505 is slidably disposed within an annular slot of the magnet assembly floating freely within the slot. The distal end of the shell 522 includes one or more extensions 524 that continue proximally from the distal end of the shell 522 and terminating at the distal mounting plate 512. In contrast to the devices of FIGS. 1 and 4, however, the device 502 does not include a separate bearing 111, 408. Rather, the interior surface of the shell 522 including its extensions 524 provides a bearing for the coil assembly 505 allowing axial movement while inhibiting radial movement. A first bearing surface 550 is defined along a distal end of the coil assembly. The first bearing surface 550 slides against the interior surface of the extensions 524 during actuation. In some embodiments, a second bearing surface 555 is provided at a proximal portion of the coil assembly 505. The second bearing surface 555 slides against the interior surface of the shell 522 during actuation.

The extensions 524 may include openings between adjacent extensions 524 as shown to reduce weight and to promote the flow of air to promote coil movement and for cooling. This configuration 502 rigidly couples the distal mounting plate 512 to the shell 522, thereby increasing rigidity of the actuator 502 and reducing if not substantially eliminating any stress/strain loading on the housing 516 (FIG. 5) caused by actuation of the device.

Figure 7:
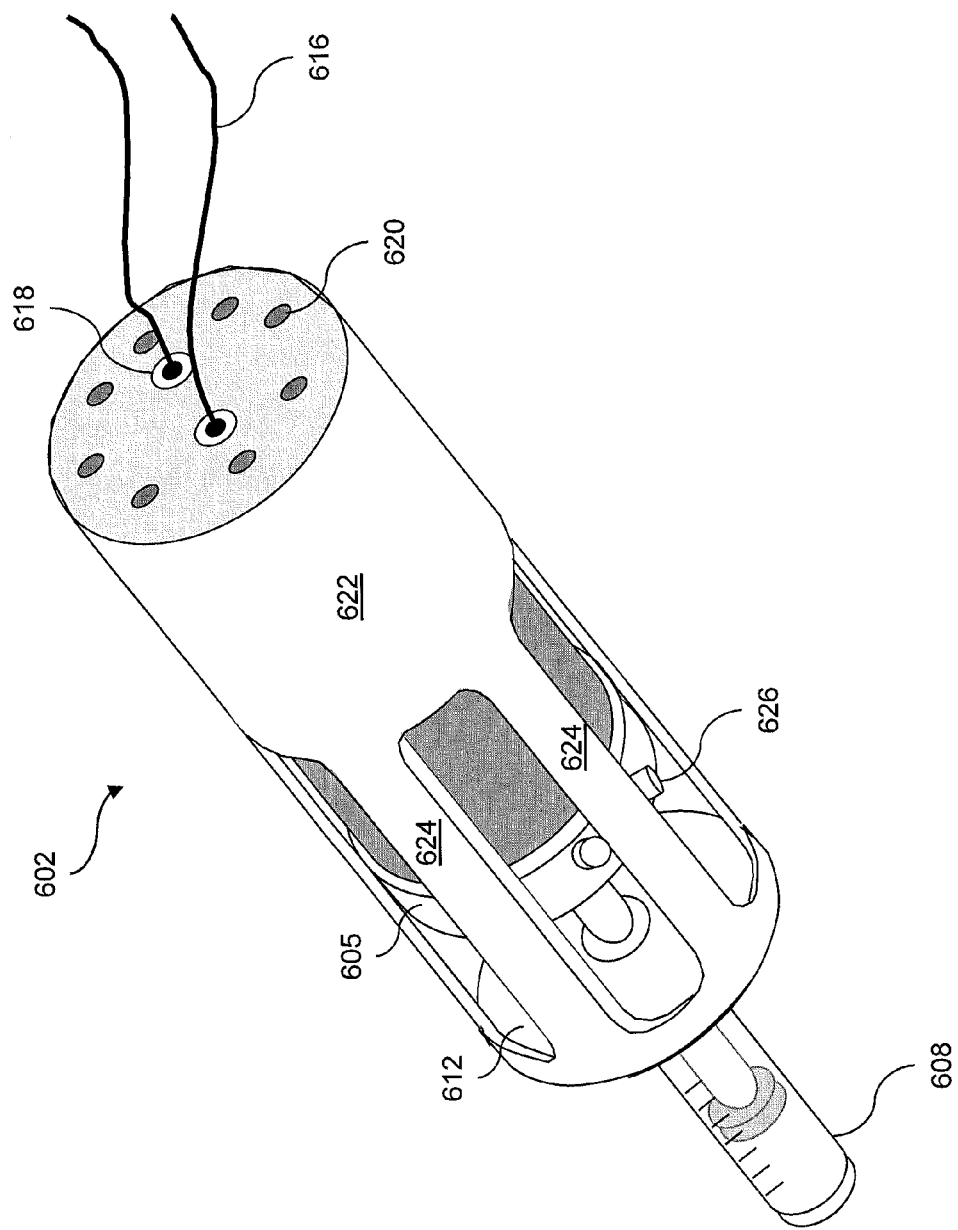
FIG. 7 is a rear perspective diagram of an embodiment of the controllable electromagnetic actuator provided in the device of FIG. 5 coupled to a syringe.

A rear perspective view of an exemplary compact Lorentz-force actuator 602 is shown in FIG. 7. The device 602 includes a magnet assembly having an external shell 622. A coil assembly 605 is slidably disposed within the shell 622, and adapted for axial translation. Multiple longitudinal extensions 624 are disposed about the axis and adapted to couple the shell 622 a mounting plate 612. Openings are provided between adjacent extensions 624. A syringe 608 is coupled to the mounting plate 612 at the distal end of the device 602. One or more guides 626 are provided to prevent rotation of the coil, each guide 626 riding along an interior edge of an adjacent extension 624. The proximal end of the device 602 includes apertures 618 through which the coil leads 616 are routed and one or more additional apertures 620 to promote air flow during actuation. In some applications a sample vial is swapped out for a drug vial between sample collection and injection. Alternatively or in addition, analysis of the sample may be performed by a separate analyzer.

Figure 8A:
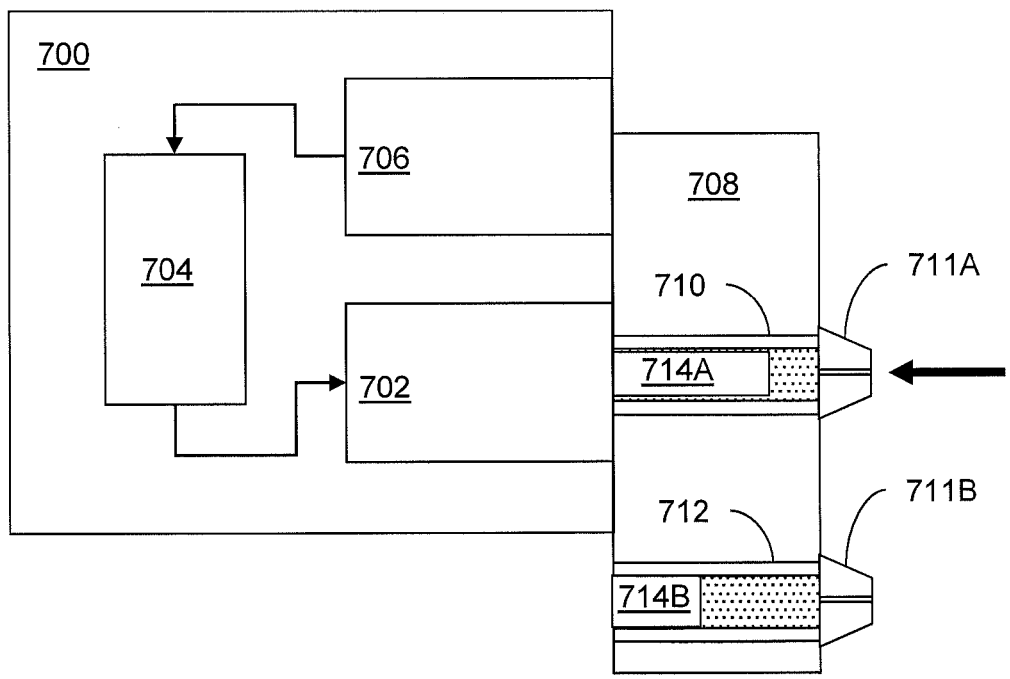
FIGS. 8A and 8B are schematic block diagrams of a needle-free transdermal transport device providing a sampling and analysis capability, respectively shown in the sampling and injection configurations.

Because the Lorentz-force actuator is bi-directional, depending upon the direction of the coil current, the same device used to inject a substance can also be used to withdraw a sample. This is a beneficial feature as it enables the device to collect a sample. Referring to FIG. 8A, an exemplary sampling, needle-free injector 700 is illustrated. The sampling injection device 700 includes a bi-directional electromagnetic actuator 702 abutting at one end a first piston 714A. A sampling nozzle 711A is coupled at the other end of a syringe 710. The actuator 702 is powered by a power source 704, such as a battery or suitably charged storage capacitor. The first piston 714A is slidably disposed within a sampling syringe 710, such that an electrical input signal applied to the actuator 702 withdraws the first piston 714A away from the sampling nozzle 711A. A sample can be collected form a biological body when the sampling nozzle 711A is placed against a surface of the body during actuation.

Figure 8B:
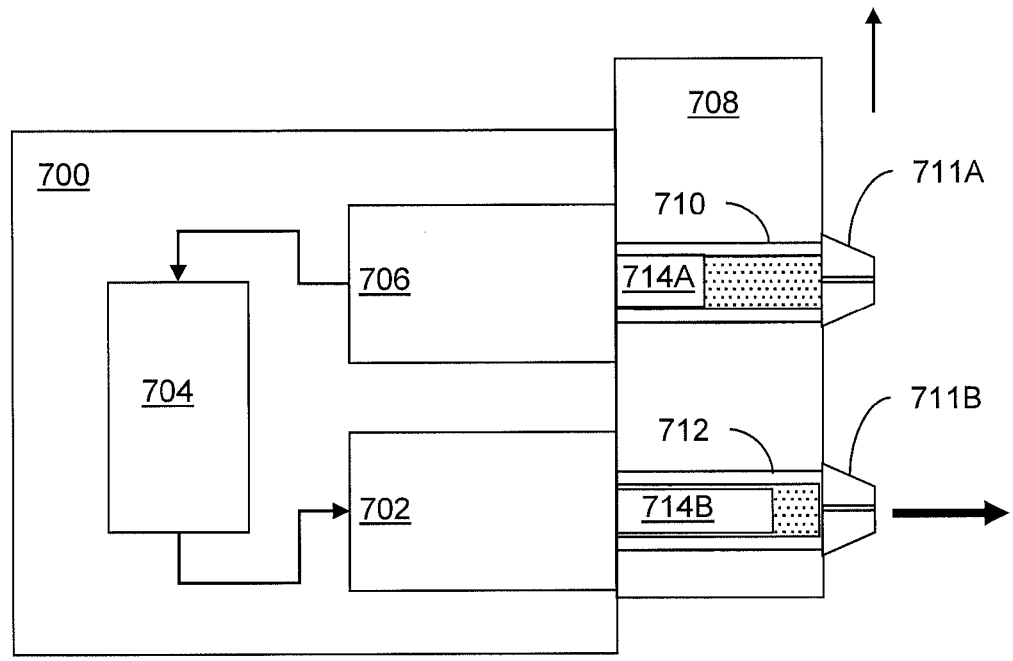

Referring now to FIG. 8B, once a sample has been collected, a movable syringe mount 708 can be re-positioned such that the sampling syringe 710 is aligned with an analyzer 706. By the same motion, a second syringe 712 having a second piston 714B and including a substance, such as a drug, is aligned with the actuator 702. The mount 708 may be a rotary mount rotating about a longitudinal axis or a linear mount as shown. The analyzer 706 provides a control signal to the power source 704 responsive to the analyzed sample. The control signal causes the actuator 702 to push the second piston 714B forward thereby expelling an amount of the substance responsive to the analyzed sample. Thus, the same device 700 can be used to both collect a sample and to inject a substance.

Figure 9A:
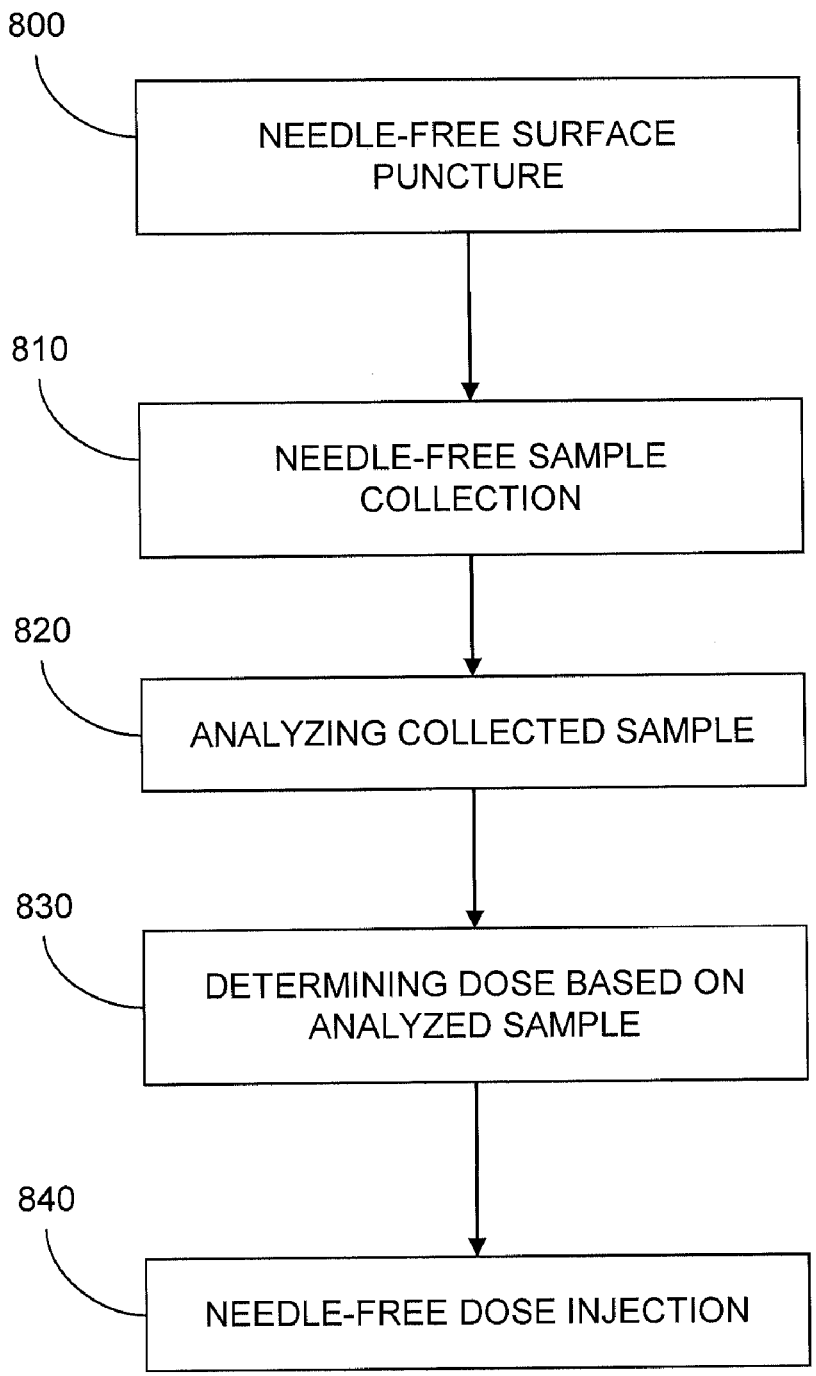
FIG. 9A is a flow diagram depicting an embodiment of a needle-free sample, analyze, and inject process.

As already described, the needle-free device can be used to collect a sample from the body. An exemplary method of collecting a sample is illustrated in the flow diagram of FIG. 9A. First, the surface is punctured using the needle free injector. (Step 800) Next, a sample is collected from the biological body again using the needle-free device. (Step 810) The collected sample is analyzed, for example to determine a physical property such as blood sugar. (Step 820) Any one or more of a number of different methods of analysis may be performed at this step. For example, analyses may include: (i) electrochemical techniques for the detection of glucose, such as a glucose oxidase test; and optical techniques, such as surface-enhanced Raman spectroscopy. The controller receives the results of the analysis and determines a dosage based on the analyzed sample. (Step 830) The determined dosage is administered to the biological body using the needle-free device. (Step 840).

Figure 9B:
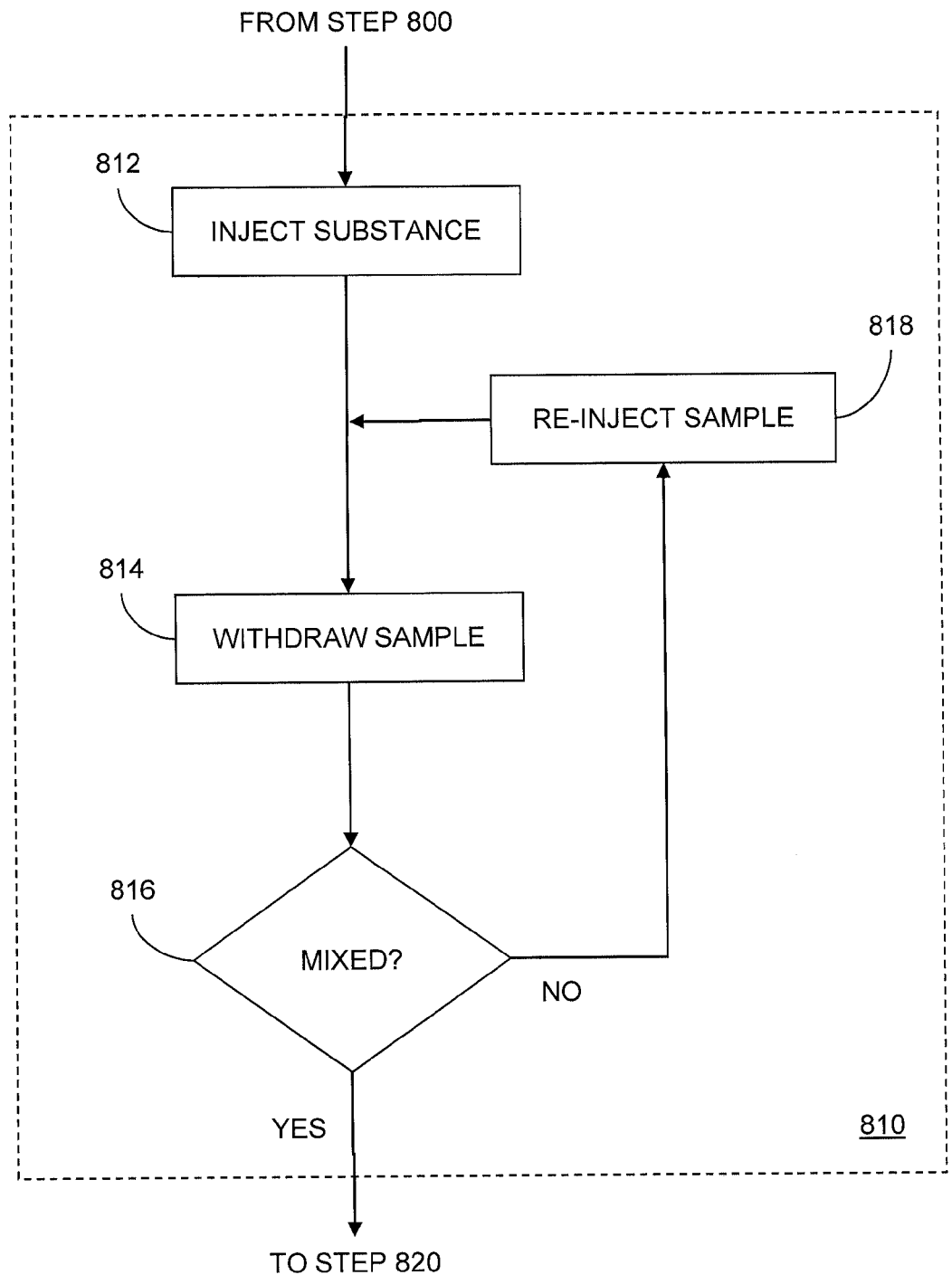
FIG. 9B is a more detailed flow diagram depicting an embodiment of an exemplary needle-free collection process.

In more detail, referring to the flow diagram of FIG. 9B, the step of needle-free sample collection (Step 810) includes first injecting a substance to pierce the skin. (Step 812) For example, saline solution can be injected to pierce the skin. Next, a sample is withdrawn using the needle-free device by sucking a sample from the biological body into a reservoir of the device. If the sample is not sufficient in volume or constitution, the withdrawn sample of saline solution and blood, tissue, and interstitial fluid is re-injected into the biological body using the need free device. (Step 818) Steps 814 through 818 can be repeated until a suitable sample or bolus is obtained. In some embodiments, determination of the sufficiency of the sample may be determined beforehand according to a prescribe number of cycles. Alternatively or in addition, sufficiency of the sample may be determined during the course of the sampling process.

Figure 10A:
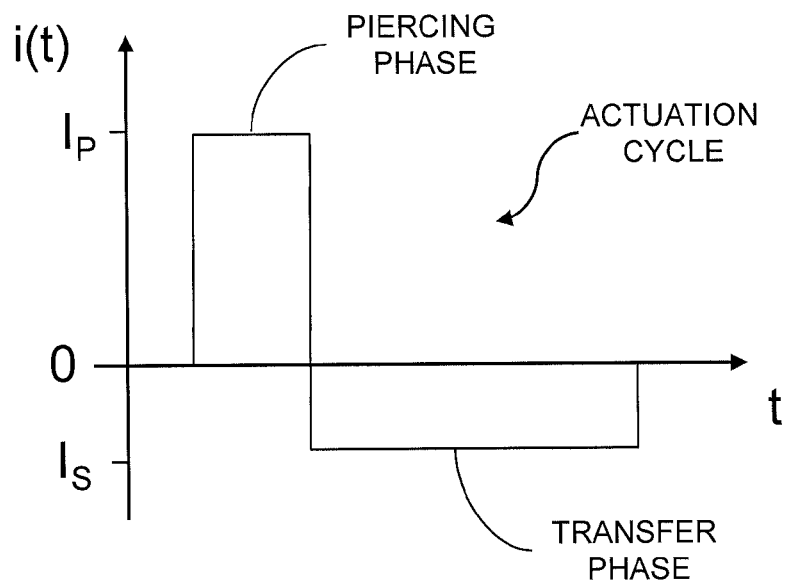
FIGS. 10A and 10B are graphs depicting current versus time profile of exemplary electrical inputs to the controllable electromagnetic actuator of FIG. 2A, 4, 5, or 8A and 8B for single and multi-sample operation, respectively.
Figure 10B:
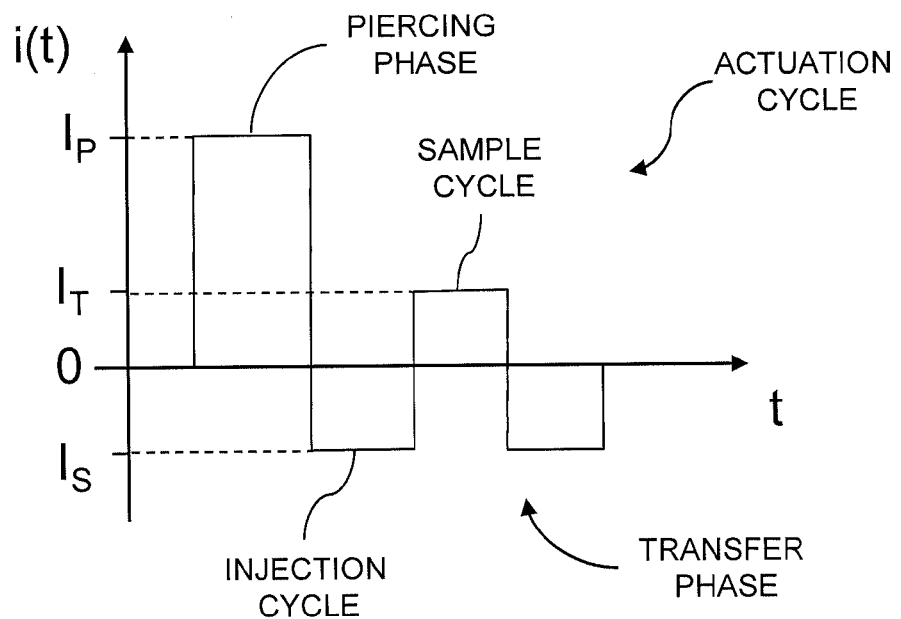

Exemplary drive currents that can be applied to the dynamically controllable electromagnetic actuator are illustrated in the plots of FIGS. 10A and 10B. Referring first to FIG. 10A, a sample actuation cycle is shown including an initial piercing phase in which a substantial positive current is applied to force a substance into the biological body creating a perforation. The piercing phase is followed by a sampling phase in which a lesser-magnitude current is applied in the opposite direction to collect a sample. Referring next to FIG. 10B, a multi cycle sample is shown in which an initial piercing phase is followed by repeated sample and re-injection phases as described in relation to FIG. 9B.

Figure 11:
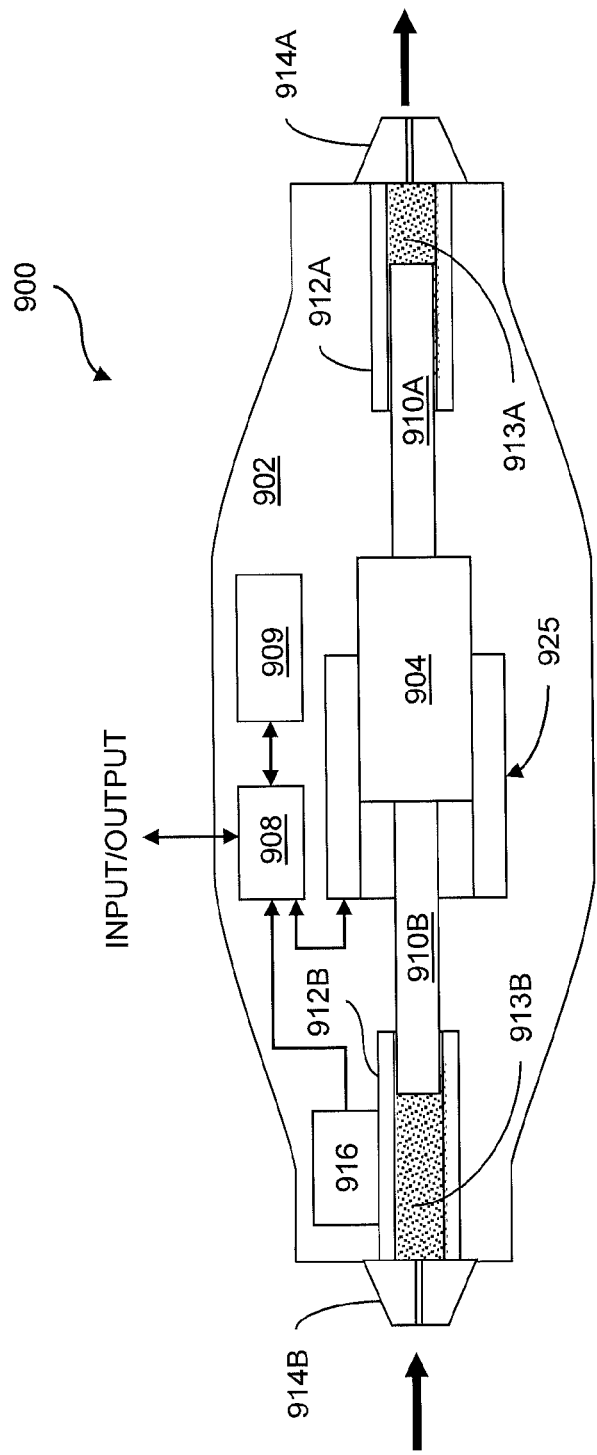
FIG. 11 is an alternative embodiment of a needle-free transdermal transfer device also providing sample and injection capabilities.

An alternative embodiment of a sampling injection device 900 is illustrated in FIG. 11. The device 900 includes two nozzles 914A, 914B each at opposing ends of the device with a controllable electromagnetic actuator 925 disposed therebetween. Each nozzle 914A, 914B is coupled at an external end of a respective syringe 912A, 912B, each syringe defining a respective reservoir 913A, 913B and each having a respective piston 910A, 910B slidably disposed therein. An internal end of each piston is coupled to a respective end of the actuator 925, such that actuation in one direction causes one plunger 910A to advance toward the distal nozzle 914A creating a pressure within the reservoir 913A adapted to inject a substance contained therein. The same actuation in the same direction causes the other plunger 910B to withdraw away from the distal nozzle 914B creating a vacuum within the reservoir 913B to withdraw a substance into the reservoir 913B.

The actuator 925 includes a movable coil assembly 904 and receives an electrical input signal from a controller 908 that is also coupled to a power source 909. In some embodiments, the device 900 includes an analyzer 916 coupled to the controller 908 for analyzing a sample collected in the sampling reservoir 913B. In operation, one end of the device can be used to collect a sample from a biological body as a result of a needle-free transfer across the surface of the biological body. The analyzer 916 may analyze the sample and provide a result to the controller 908. The controller 908 may determine the parameters for a dosage of a substance to the biological body based on the analyzed sample.

The other end of the device can be used to administer a dosage of a substance to the biological body. The controller then provides an electrical input form the power source 909 to the actuator 925, possibly under the control of a local or remote operator through an input/output interface. The actuator 925 moves a piston in the same direction according to the received input, creating a pressure and causing an injection through the injecting end of the device 900.

In some embodiments, it is advantageous to provide a controllable needle-free injection device 1000 capable of administering multiple injections and/or samples in succession. Thus, actuation cycles occur with relatively short time delay between cycles adjacent. Such a device can be referred to as a multi-shot needle-free injection device. Multi-shot injections can occur within 30 milliseconds to 50 milliseconds per cycle, with an actuation (i.e., injection) cycle 10 milliseconds. Some multi-shot devices have a capability to deliver up to 500 injections per drug vial.

Figure 12:
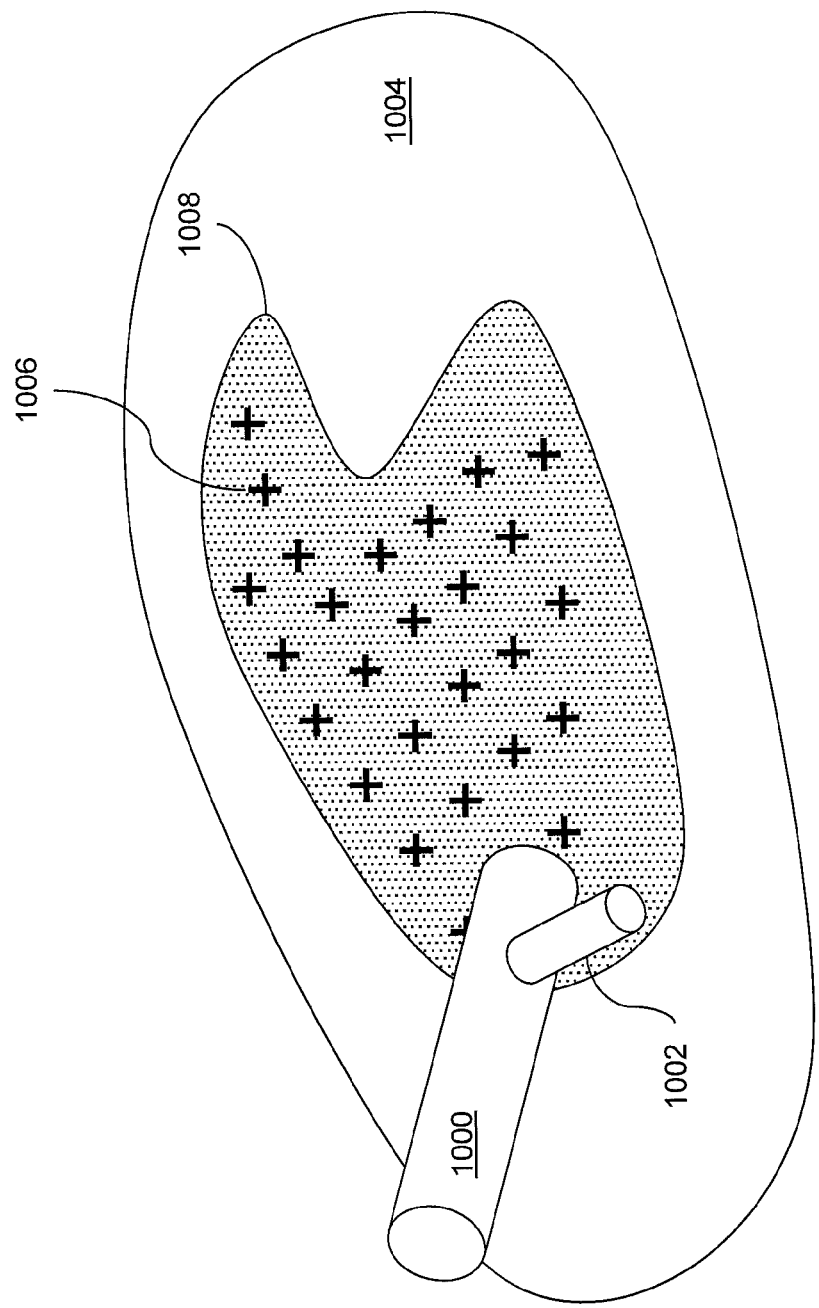
FIG. 12 is a perspective diagram showing surface treatment using a multi-shot needle-free transdermal transport device.

For example, referring to the schematic diagram of FIG. 12, a multi-shot, needle-free injection device 1000 includes an attached reservoir or ampoule 1002. The device 1000 is applied to the surface of a biological body 1004 and a transdermal transfer is initiated a first location 1006 at which the tip of the device 1000 is placed. The process can be repeated at other locations in a general proximity with respect to each other thereby treating a substantial surface region 1008 of the biological body. In other applications, the same multi-shot device 1000 can be used to transdermally transfer a substance in each of multiple different biological bodies. Such applications would include inoculating a group of animals, one after another.

Figure 13:
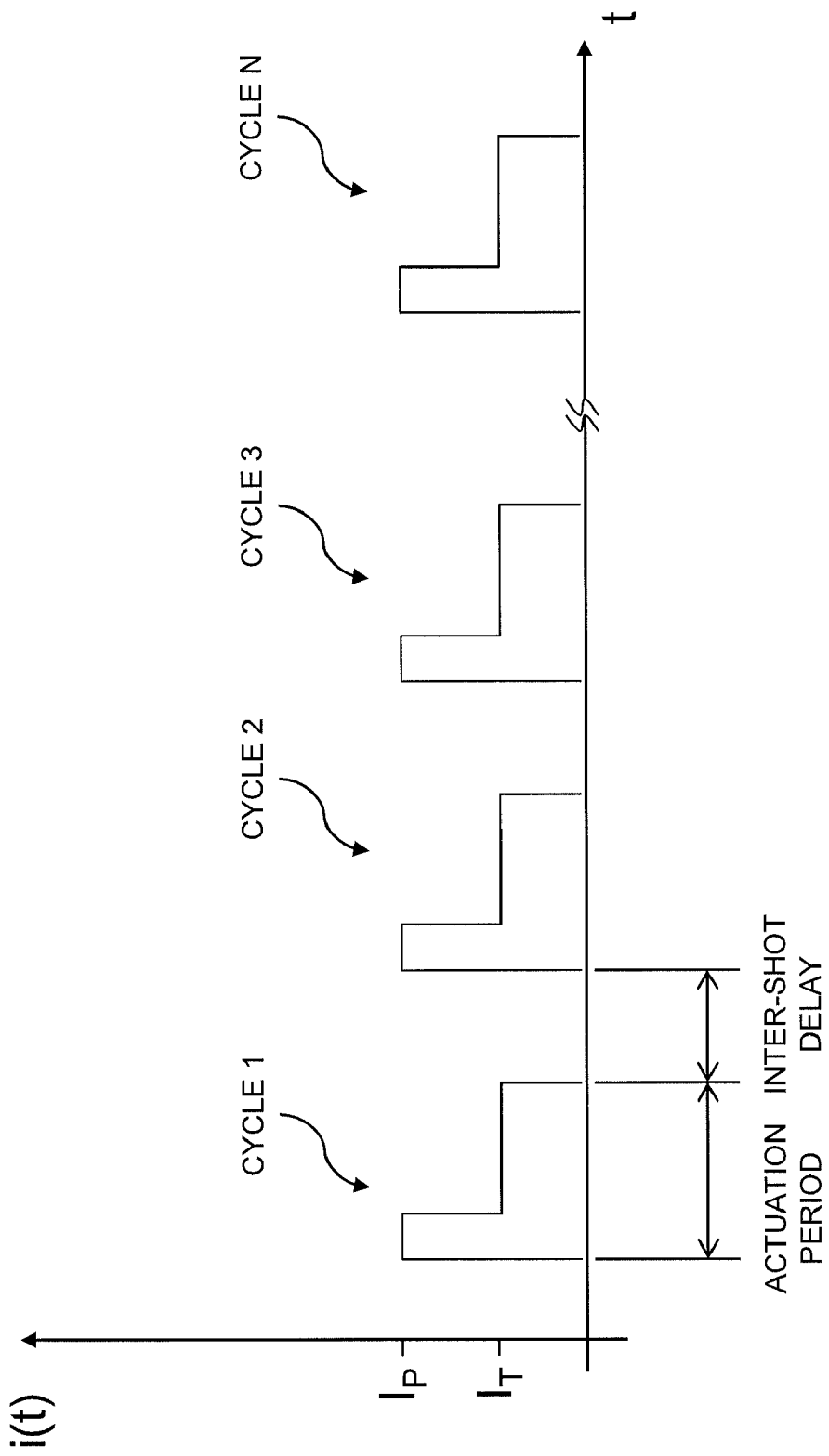
FIG. 13 is a graph depicting current-versus-time profile of exemplary electrical inputs to the controllable electromagnetic actuators of FIG. 2A, 4, 5, 8A or 8B for multi-shot transfers.

A plot of an exemplary coil drive current versus time for a multi-shot application is illustrated in FIG. 13. The current profile of an individual actuation cycle or period can be similar to any of those described earlier in relation to FIGS. 3, 10A and 10B separated by a user-selectable inter-shot delay. Although the same general input waveform is illustrated for each cycle, the device is capable of initiating different waveforms for each cycle.

Figure 14B:
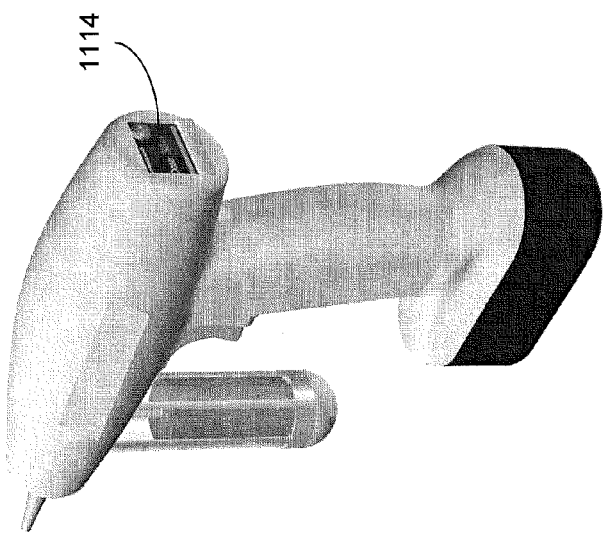
FIGS. 14A and 14B are front and rear perspective diagrams of an exemplary portable needle-free transdermal transport device.
Figure 14A:
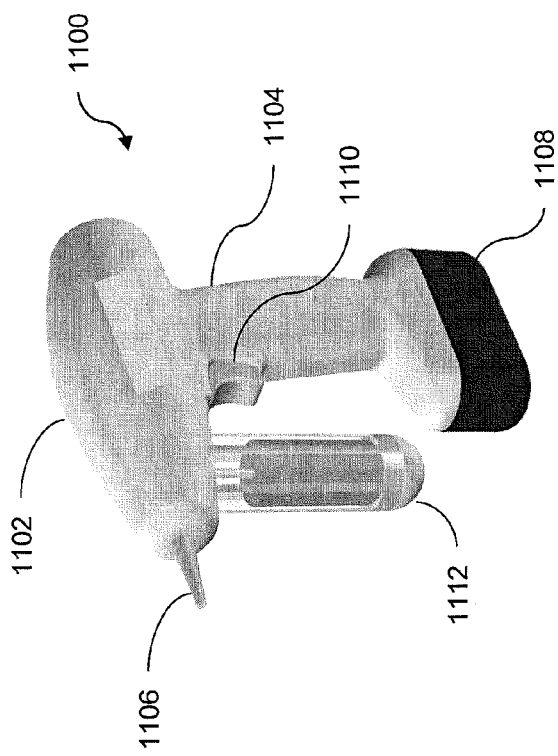

An exemplary portable, multi-shot injection device 1100 is illustrated in FIGS. 14A and 14B. The device 1100 includes a housing 1102 having a handle section 1104 that may include a trigger 1110. The device also includes a nozzle 1006, a reservoir or ampoule 1112 and a self-contained power source 1108. In some embodiments, the device 1100 also includes a user interface 1114.

Referring to the power source 106 in more detail, it is possible to charge a rechargeable power source, such as a rechargeable battery or storage capacitor. For example, recharging can be accomplished with solar cells, a dynamo, or inductive coupling. For example, the coil assembly 104 can be used in the inductive coupling to an external power source, the coupled source creating an electrical current within the coil assembly 104, usable to charge the power source 106.

In some embodiments, the device can be recharged using the electromagnetic actuator 125 itself. That is, mechanical movement of the coil assembly 104 through the magnetic field provided by the magnet assembly 105 (as might be accomplished by shaking or vibrating the device 100) produces an electrical current within the coil. The coil assembly 104 may be coupled to the power source 106 through a regulator or other suitable recharging circuit. Thus, electrical current induced within the coil assembly 104 by its movement through the magnetic field can be used to recharge the power source 106.

Figure 15:
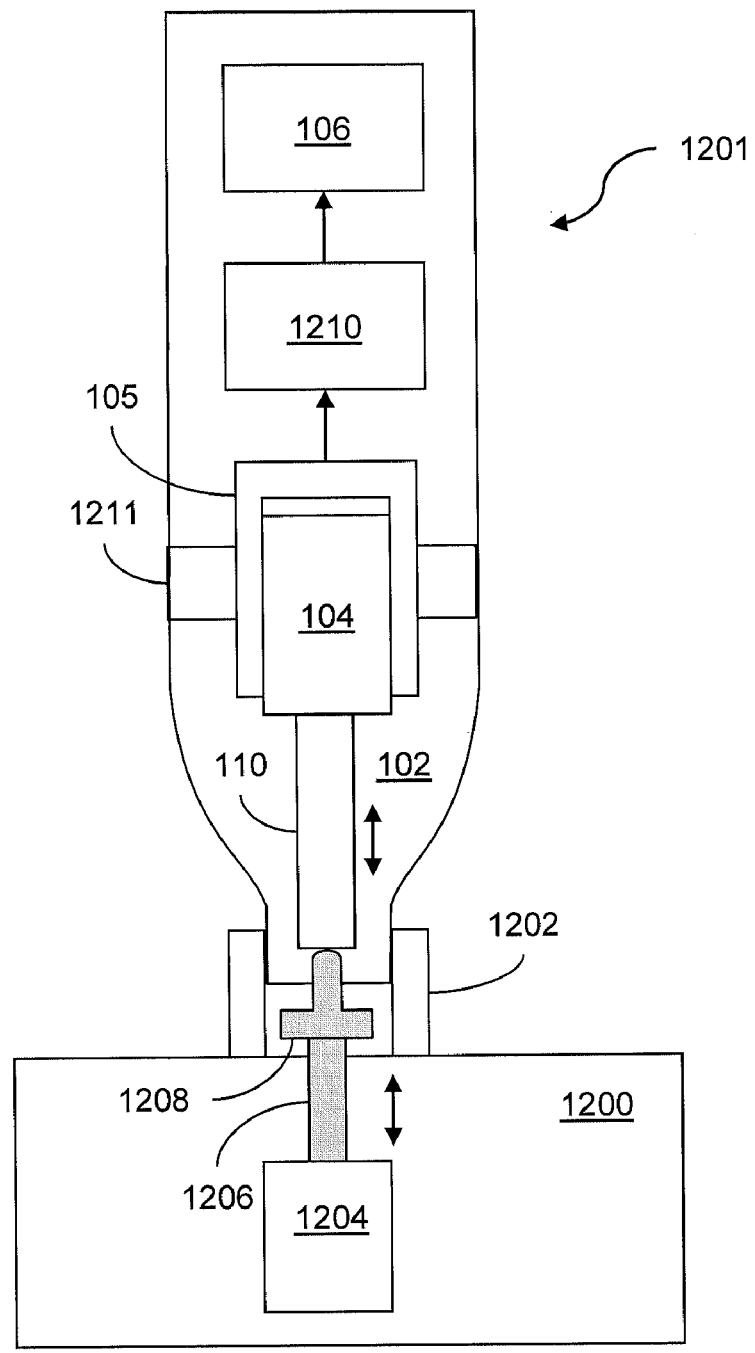
FIG. 15 is a schematic block diagram of a mechanical recharging unit coupled to a rechargeable needle-free transdermal transport device for recharging an internal power source.

An exemplary mechanical recharging device is illustrated in FIG. 15. The mechanical recharging unit 1200 includes a mechanical transducer, such as a vibrator 1204, that oscillates a shaft 1206 back and forth. The shaft is coupled at one end to the vibrator 1204 and at the other end to an adapter fitting 1208 adapted to engage the forced-transfer member 110 of the device 1201. The recharging unit 1200 also includes a mounting flange 1202 adapted to hold a device in engagement with the vibrator 1204 during a recharging period. As shown, a syringe is first removed so that the coil assembly can be oscillated through the magnetic field producing an electrical current in the coil 104. The resulting current can be fad back into the power source 106 through a power conditioner 1210. The power conditioner 1210 can include one or more of a rectifier, a voltage regulator, a filter, and a recharging unit. As shown, the magnet assembly 105 is coupled to the housing 102 through a mounting 1211, such that the magnet remains fixed with respect to the moving coil assembly 104.

The controllable nature of such a transdermal transfer device lends itself to automatic, or robotic injection. First, a forceful needle-free injection may be used to inject through the skin of a biological body, such as the relatively thick hide of a large mammal, such as a cow. As the injection is needle-free, there is no chance of a needle breaking within an animal, should the animal move during the course of an injection. Further, because a forceful needle-free injection can be accomplished in a fraction of a second, the duration of time during which an animal must remain immobile is greatly reduced. Thus, a mere bump of a nozzle on an animal combined with a momentary release may occur in such a short period of time, that it may even be done while the animal is mobile.

Figure 16:
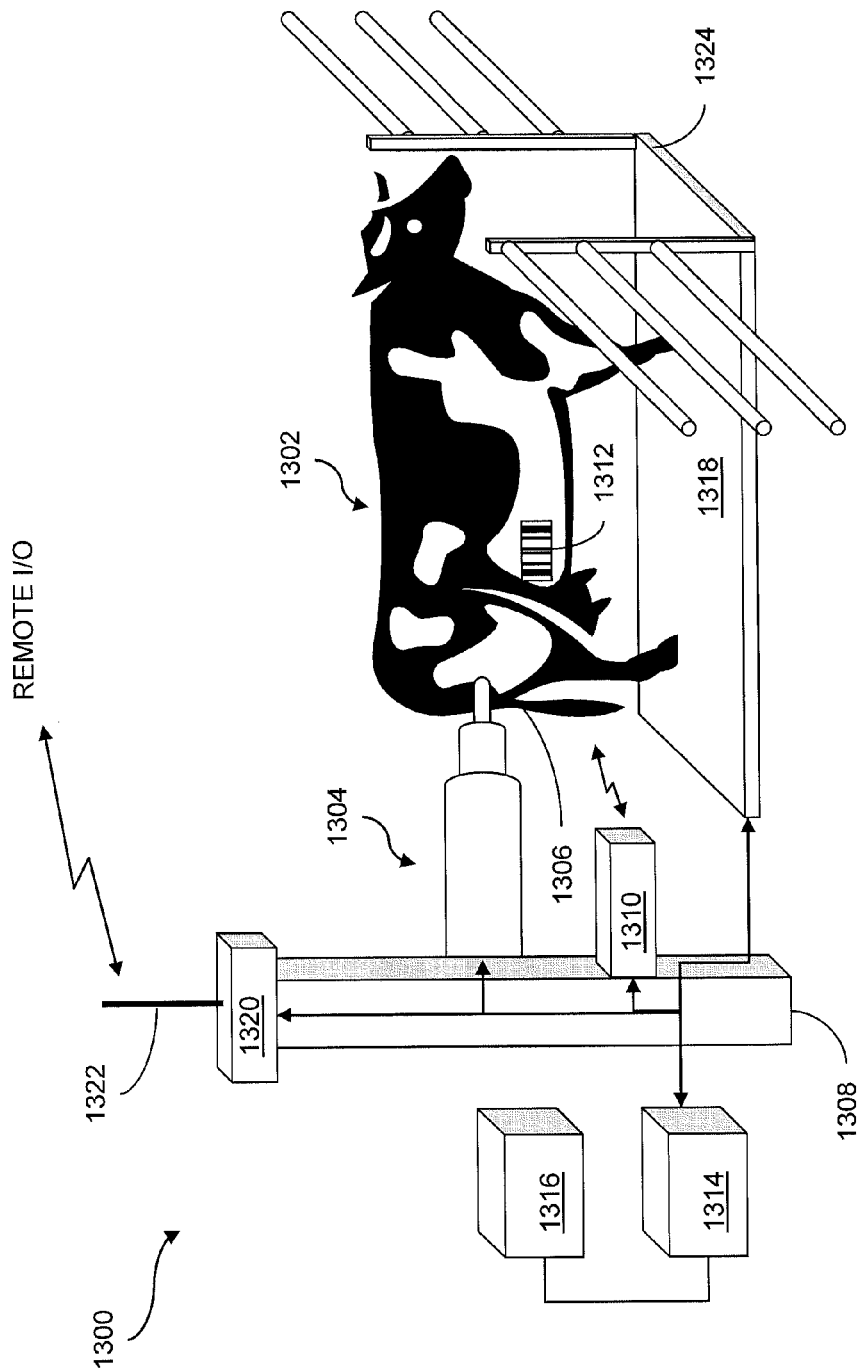
FIG. 16 is a schematic block diagram of an automated needle-free transdermal transport system adapted to automatically administer a needle-free transfer to an animal.

An exemplary needle-free injection system for administering a controlled dose of a substance to an animal is illustrated in FIG. 16. The system includes a needle-free transdermal transport device 1306 disposed at a distal end of an extendable arm 1304. The proximal end of the arm 1304 may be connected to a rigid mount, such as a post or frame 1308. A sensor 1310 may also be provided to identify an animal prior to administering a transdermal transfer. For example, the animal 1302 can include an identifying mark 1312, such as a bar-code tag or a radio frequency identification (RFID) tag. The sensor 1310 can therefore include an interrogator adapted to read a bar-code or RFID tag. The sensor 1310 and the transdermal transport device 1306 are both coupled to a controller 1314, which may include a processor. A power source 1316 is also coupled to the transdermal transfer device 1306 through the controller 1314.

In some embodiments, the device includes another animal sensor, such as a force plate 1318 adapted to sense a physical property of the animal such as its weight. A guide, such as a gate 1324 can be provided to suitably position the animal 1302 during identification and dosage. The controller 1314 also receives an input from the sensor 1318 and generates a dosage control based on the animal identification and weight. For example, a growth hormone could be administered to a particular animal based on its identification and weight.

In some embodiments, the system also includes a communications interface 1320. The communications interface can include a wireless interface 1322, such as the wireless communications interface discussed above in relation to FIG. 1. Thus, the system can communicate with a remote user, processor, and/or database.

The operational features offered by the dynamically controllable Lorentz-force actuator support numerous and varied treatment options. Combining both a forceful injection capability with controllability, the same controllable needle-free transdermal transport device can be used to deliver varied injections. For example, the device can be used non-invasively to deliver intradermally into a surface layer or the skin, between different biological layers (e.g., along a cleavage plane), or a subcutaneous injection administered to the subcutis, a layer of skin directly below the dermis and epidermis. Non-axial needle-free injections are described in U.S. patent application entitled "Surface Injection Device" filed on Feb. 10, 2006 under Ser. No. 11/351,887, incorporated herein by reference in its entirety. The device may also be used to deliver an intramuscular injection administering a substance directly into a muscle. Still further, the device may be used to deliver intravenous infusion administering a drug directly into the bloodstream via a vein.

Figure 17:
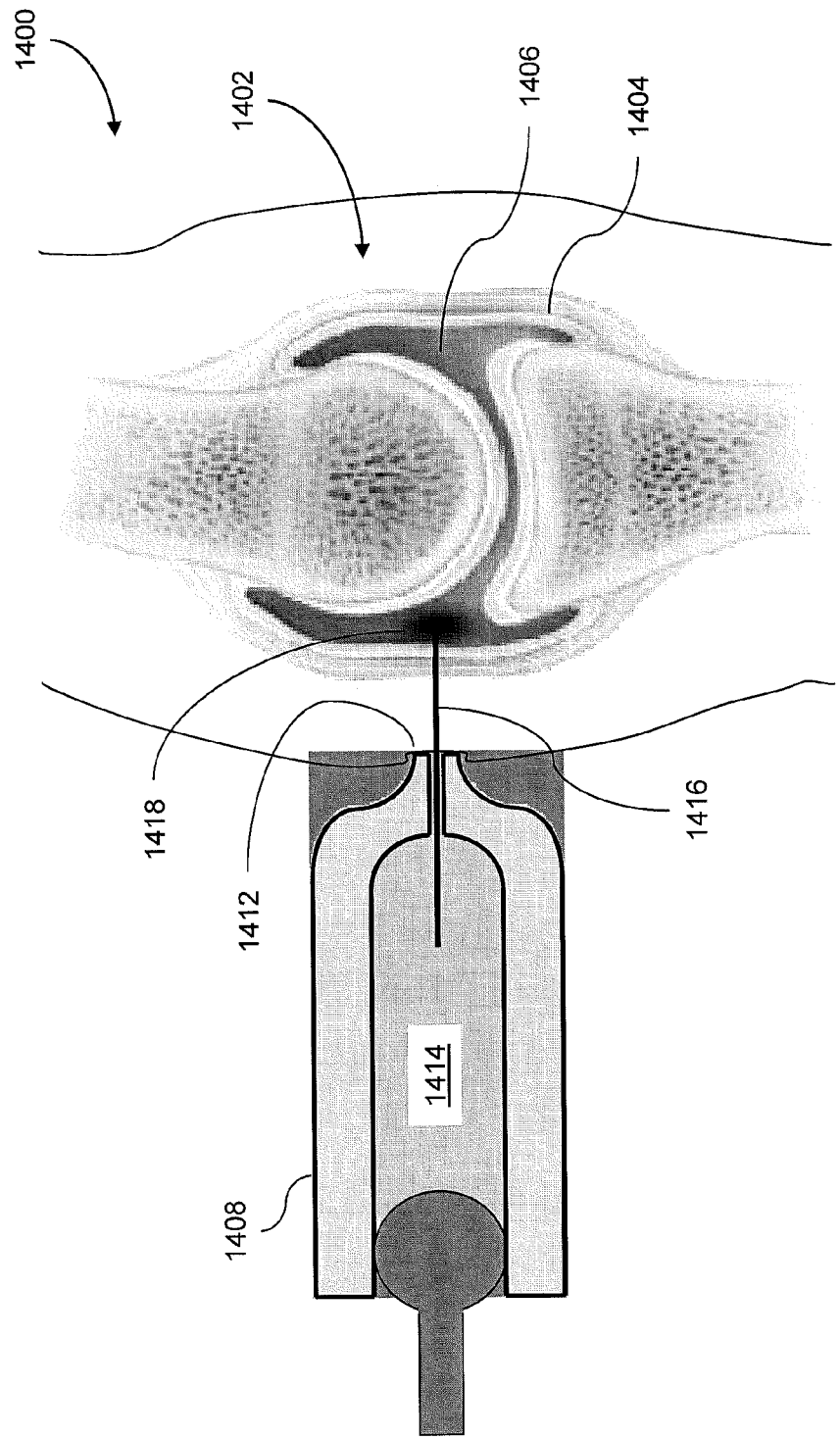
FIG. 17 is a schematic diagram of a needle-free transdermal transport device injecting a substance into an animal's joint.

An exemplary application for injecting a substance into an anatomical joint is illustrated in FIG. 17. A portion of a human knee 1400 is shown as an example of a synovial joint 1402. A synovial joint 1402 includes a viscous fluid 1406 which is contained inside the "synovial" membrane 1404, or "joint capsule. In some treatments it is desirable to inject a substance into the viscous fluid 1406. This requires a relatively deep injection also penetrating the synovial membrane 1404. Heretofore, such an injection required the use of larger gauge needles to prevent bending or breaking of the needle. Unfortunately, the larger diameter needle tended to increase pain and discomfort to the patient. Using the controllable electromagnetic needle-free device, it is possible to accomplish such an injection delivering a substance 1414. Namely, the substance 1414 stored in a syringe 1408 is expelled through a nozzle 1412. A narrow jet is formed by the nozzle 1412, directing a stream 1416 of the substance along a straight line path to a desired depth. Thus, the stream 1416 can be directed to the interior region of the joint 1402 piercing the synovial membrane 1404 and delivering the substance 1418 with less pain and without bending.

Figure 18:
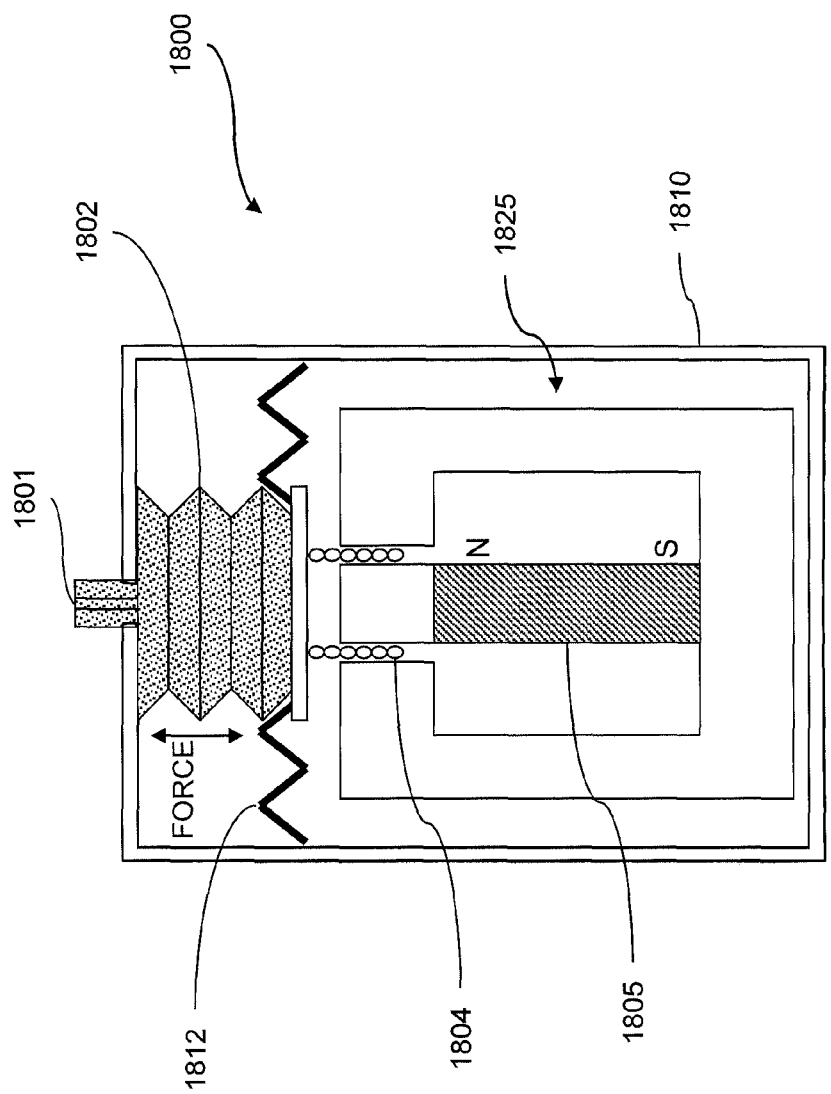
FIG. 18 is a schematic block diagram of an alternative needle-free transdermal transport device including a bellows reservoir.

An alternative embodiment of a controllable needle-free injection device 1800 shown in FIG. 18 including a bellows 1802 forming a reservoir therein. An electromagnetic actuator 1825 either compresses or expands the bellows 1802, depending upon the direction of the electrical input current. A nozzle 1801 adapted for needle-free injection is in fluid communication with the bellows chamber 1802 such that a formulation stored within the chamber 1802 is forced through the nozzle 1801 when the bellows 1802 is compressed. The nozzle 1801 is generally held in a fixed relationship with respect to the stationary portion of the actuator 1825, such the bellows is compressed between the movable portion of the actuator 1825 and the nozzle 1801.

The bellows chamber 1802 can be configured for quick and easy removal and replacement within the injection device 1800. For example, a bellows chamber 1802 can be inserted into and removed from a side of a housing 1810. The housing 1810 can include a mechanical fastener that secures the bellows chamber 1802 to the coil assembly 1804. For example, the mechanical fastener can include a blade (not shown) configured to engage a complementary notch in the bellows chamber. Alternatively or in addition, specially-configured bellows can be used that are axially compressible while being otherwise rigid in non-axial directions.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for transferring a substance across a surface of a body comprising the steps of:
    applying an electrical input to a controllable Lorentz force electromagnetic actuator comprising a moving coil assembly and a stationary magnet assembly;
    producing with the electromagnetic actuator a mechanical force corresponding to the electrical input;
    applying the mechanical force to a reservoir coupled at one end to a nozzle, the mechanical force producing a pressure within the reservoir, a magnitude of the pressure varying with the mechanical force and causing transfer of the substance across the surface of the body;
    sensing, during the transfer of the substance, a physical property; and
    varying the applied electrical input during the transfer of the substance responsive to the sensed physical property to produce a corresponding variation in the applied mechanical force.

2. The method of claim 1, wherein the applied force produces a positive pressure ejecting at least a portion of the substance from the reservoir through the nozzle, the ejected substance producing a jet having sufficient velocity to pierce the surface of the body.

3. The method of claim 2, wherein the applied force is bi-directional, depending upon the applied electrical input producing a positive pressure responsive to a first electrical input and a negative pressure responsive to a second input, the negative pressure creating a vacuum within the reservoir, the vacuum causing transfer of the substance from the body to the reservoir.

4. The method of claim 1, wherein the step of applying an electrical input comprises applying a first electrical input to the controllable electromagnetic actuator producing therewith a positive force ejecting a portion of the substance through the nozzle at a sufficient velocity.

5. A method for transferring a substance across a surface of a body comprising the steps of:
    providing the substance in a reservoir having a piston driven by a Lorentz force actuator comprising a moving coil assembly and a stationary magnet assembly;
    applying an electrical current to the Lorentz force actuator, the current inducing a force to drive the piston and transfer the substance from the reservoir across the surface of the body; and
    varying the applied electrical current during the transfer of the substance to produce a corresponding variation in the force.

6. The method of claim 5, further comprising:
    sensing, during the transfer, a physical property; and
    varying the applied electrical current during the transfer of the substance responsive to the sensed physical property.

7. The method of claim 5, wherein the force produces a positive pressure within the reservoir ejecting at least a portion of the substance from the reservoir through a nozzle coupled to the reservoir, the ejected substance producing a jet having sufficient velocity to pierce the surface of the body.

* * * * *

UNITED STATES PATENT AND TRADEMARK OFFICE
CERTIFICATE OF CORRECTION

PATENT NO. : 8,328,755 B2  
APPLICATION NO. : 12/906525  
DATED : December 11, 2012  
INVENTOR(S) : Ian W. Hunter et al.

Page 1 of 1

It is certified that error appears in the above-identified patent and that said Letters Patent is hereby corrected as shown below:

On the Title page in the Related U.S. Application Data item (60), delete:

"Division of application No. 11/354,279, filed on Feb. 13, 2006, now U.S. Pat. No. 7,833,189, which is a continuation of application No. 11/352,916, filed on Feb. 10, 2006, now abandoned."

and insert:

--Division of application No. 11/354,279, filed on Feb. 13, 2006, now U.S. Pat. No. 7,833,189, which is a continuation-in-part of application No. 11/352,916, filed on Feb. 10, 2006, now abandoned.--

Signed and Sealed this
Twelfth Day of February, 2013

Teresa Stanek Rea
*Acting Director of the United States Patent and Trademark Office*